US005607659A

United States Patent [19]
Gustavson et al.

[11] Patent Number: 5,607,659
[45] Date of Patent: Mar. 4, 1997

[54] DIRECTED BIODISTRIBUTION OF RADIOLABELLED BIOTIN USING CARBOHYDRATE POLYMERS

[75] Inventors: Linda M. Gustavson, Seattle; Alan R. Fritzberg, Edmonds, both of Wash.

[73] Assignee: NeoRx Corporation, Seattle, Wash.

[21] Appl. No.: 482,788

[22] Filed: Jun. 7, 1995

Related U.S. Application Data

[63] Continuation of Ser. No. 12,533, Feb. 2, 1993, abandoned.

[51] Int. Cl.$^6$ .................................................. A61K 51/04
[52] U.S. Cl. ........................................... 424/1.73; 514/387
[58] Field of Search ........................... 424/1.73; 514/387

[56] References Cited

U.S. PATENT DOCUMENTS

| | | | |
|---|---|---|---|
| 4,385,046 | 5/1983 | Milbrath et al. | 424/1 |
| 4,732,974 | 3/1988 | Nicolotti et al. | 530/390 |
| 4,849,208 | 7/1989 | Stavrianopoulos | 424/1.1 |
| 4,855,353 | 8/1989 | Kurami et al. | 525/54.1 |
| 4,863,713 | 9/1989 | Goodwin et al. | 424/1.1 |
| 4,985,233 | 1/1991 | Klaveness et al. | 424/9 |
| 5,026,785 | 6/1991 | Mage et al. | 525/329.4 |
| 5,053,520 | 10/1991 | Dean et al. | 540/474 |
| 5,057,313 | 10/1991 | Shih et al. | 424/85.91 |
| 5,153,265 | 10/1992 | Shadle et al. | 525/54.1 |
| 5,162,505 | 11/1992 | Dean et al. | 530/391.5 |
| 5,420,105 | 5/1995 | Gustavson et al. | 514/2 |
| 5,482,698 | 1/1996 | Griffiths | 424/141 |
| 5,525,338 | 6/1996 | Goldenberg | 424/178.1 |

FOREIGN PATENT DOCUMENTS

| | | |
|---|---|---|
| 268707 | 6/1988 | European Pat. Off. . |
| WO91/15242 | 10/1991 | European Pat. Off. . |
| 2225579 | 6/1990 | United Kingdom . |

OTHER PUBLICATIONS

International Search Report issued in PCT/US94/01036.
Torchilin et al., *Journal of Controlled Release* vol. II, pp. 297–303, Jan. 1990.
Armitage et al., *Bioconjugate Chem.*, vol. 1, pp. 365–374, 1990, "Polymeric Contrast Agents for Magnetic Resonance Imaging: Synthesis and Characterization of Gadolinium Diethylenetriaminepentaacetic Acid Conjugated to Polysaccharides".
Krenning et al., *J. Nucl. Med.*, vol. 33, pp. 652–658, 1992, "Somatostatin Receptor Scintigraphy with Indium–111–D–Phe–1–Octreotide in Man: Metabolism, Dosimetry and Comparison with Iodine–123–Tyr–3–Octreotide".
Midoux et al., *Bioconjugate Chem.*, vol. 3 pp. 194–199, 1992, "Activation of Mouse Macrophages by Muramyl Dipeptide Coupled with an Anti–Macrophage Monoclonal Antibody".

Torchilin et al., *J. Controlled Release*, vol. 11, pp. 297–303, 1990, "Antibody–Linked Chelating Polymers for Immunoimaging In–Vivo".
Persiani et al., *Carcinogenesis*, vol. 12, pp. 1149–1152, 1991, "Polylysine conjugates of Bowman–Birk protease inhibitor as targeted anti–carcinogenic agents".
Khaw et al., *J. Nucl. Med.*, Abstract No. 461, vol. 33, p. 934, 1992, "A New Approach to Imaging Experimental Atherosclerotic Lesions with Monoclonal Antibody Z3D3": Enhanced Targeting Utilizing Antibody–Avidin–Biotin Interactions.
Gansow, *Nucl.*, Abstract No. 9, 1992 "Medical Application of Generator Produced Radionuclides: Current Clinical Results with Antibodies and Future Directions".
del Rosario et al., *J. Nucl. Med.*, Abstract No. 356, vol. 32, p. 993, 1991 "Bolton–Hunter and Biotin Derivatized Polylysine: A new Multi–valent Peptide Reagent for In–Vivo Pre–targeting with Streptavidin Conjugates."
Hurwitz et al., *Bioconjugate Chem.*, vol. 1. pp. 285–290, 1990, "A Conjugate of 5–Fluorouridine–Poly(L–lysine) and an Antibody Reactive with Human Colon Carcinoma".
Takakura et al., *Pharmaceutical Research*, vol. 7, pp. 339–346, 1990, "Disposition Characteristics of Macromolecules in Tumor–Bearing Mice".
Pithayanukul et al., *Pharm. Bull.*, vol. 37, pp. 1587–1590, 1989, "In Vitro pH–Dependent Drug Release from $N^4$–(4–Carboxybutyryl)–1–B–arabinofurano–sylcytosine and Its Conjugate with Poly–L–lysine or Decylenediamine–dextran T70".
Manabe et al., *Biochemical and Biophysical Research Communications*, vol. 115, pp. 1009–1014, 1983, "Production of Monoclonal Antibody–Bleomycin Conjugate Utilizing Dextran T–40 and the Antigen–Targeting Cytotoxicity of the Conjugate".
Hurwitz et al., *J. Med. Chem.*, vol. 28, pp. 137–140, 1985, "The Covalent Linking of Two Nucleotide Analogues to Antibodies".
Hurwitz et al., *J. Applied Biochem.*, vol. 2, pp. 25–35, 1980, "Soluble Macromolecules as Carriers for Daunorubicin".

*Primary Examiner*—Gary E. Hollinden
*Assistant Examiner*—Lara E. Chapman
*Attorney, Agent, or Firm*—Burns, Doane, Swecker & Mathis, LLP

[57] ABSTRACT

The present invention provides methods for directing the biodistribution of molecules that are not generally specifically excreted via the renal pathway to renal excretion. The methods employ conjugates or complexes containing a directed biodistribution molecule (DBM) and one or more bound molecules, wherein the biodistribution of the conjugate or complex is directed to renal excretion in vivo by the DBM component thereof.

6 Claims, 3 Drawing Sheets

1

DIRECTED BIODISTRIBUTION OF RADIOLABELLED BIOTIN USING CARBOHYDRATE POLYMERS

This application is a continuation of application No. 08/012,533, filed Feb. 2, 1993, now abandoned.

TECHNICAL FIELD OF THE INVENTION

The present invention is directed to directed biodistribution molecules (DBMs) that direct the biodistribution of administered small molecules to improve the performance thereof in diagnostic or therapeutic protocols. More specifically, the present invention is directed to DBMs that mask or override the biodistribution properties of small molecules, such that the small molecule excretion mimics DBM excretion. Directed biodistribution to renal excretion as well as DBM/small molecule conjugates or complexes designed for renal excretion are discussed.

BACKGROUND OF THE INVENTION

Radiolabeled antibodies are exemplary targeted moieties that are used in a variety of diagnostic and therapeutic medical procedures. The increased specificity of monoclonal antibodies, compared to polyclonal antibodies, makes them more useful for delivering diagnostic or therapeutic agents such as radioisotopes to desired target sites in vivo. A monoclonal antibody specific for a desired type of target cells (e.g., tumor cells) may be used to deliver a therapeutic radionuclide-antibody conjugate to target cells, thereby causing the eradication of the undesired target cells. Alternatively, a monoclonal antibody having a diagnostically effective radionuclide attached thereto may be administered, whereupon the radiolabeled antibody localizes to target tissue. Conventional diagnostic procedures then may be used to detect the presence of target sites within the patient.

One method for radiolabeling proteins such as antibodies involves attachment of radionuclide metal chelates thereto. Chelates having a variety of chemical structures have been developed for this purpose. The usefulness of such chelates is dependent upon a number of factors including the stability of radionuclide binding within the chelate and the reactivity of the chelate with the desired protein. The efficiency of the radiolabeling process producing the radionuclide metal chelate is also important. Another consideration is the biodistribution of the radiolabeled antibody and catabolites thereof in vivo.

Image contrast achievable in diagnostic applications of this technology is limited by the ratio of radioactivity localized to the tumor and radioactivity associated with normal tissue. A limitation in the use of radioimmunotherapy in the treatment of cancer is dose limiting toxicity to normal organs. Biodistribution studies in mice have shown that compounds, such as radiolabeled small molecules, are rapidly cleared from the blood, taken up by the liver and excreted into the intestines. Such hepatobiliary excretion poses additional problems with respect to conventionally labeled antibodies, because antibody-chelate-radionuclide conjugates are metabolically degraded to form stable chelate-lysine adducts that show significant intestinal accumulation.

Certain peptides (e.g., somatostatin and derivatives thereof) have been employed as targeting agents to direct active agents to protein receptor-rich tumor targets. Hepatobiliary clearance of these radiolabeled peptides is also problematic. Also, radiolabeled ligand (e.g., biotin) derivatives used in pretargeting protocols have also exhibited undesirable hepatobiliary excretion.

SUMMARY OF THE INVENTION

The present invention provides methods for directing the biodistribution of molecules that are not generally specifically excreted via the renal pathway to renal excretion. The methods employ conjugates or complexes as described below.

The present invention provides conjugates or complexes containing a directed biodistribution molecule (DBM) and one or more bound molecules, wherein the biodistribution of the conjugate or complex is directed to renal excretion in vivo by the DBM component thereof. Small molecules, including targeting moieties, such as oligonucleotides and peptides, drugs, ligands, anti-ligands and chelates, are characterized by improved biodistribution characteristics when conjugated to DBMs in accordance with the present invention. Preferably, conjugates or complexes of the present invention include a diagnostic or therapeutic active agent. Optionally, such conjugates or complexes exhibiting improved biodistribution in accordance with the present invention may include larger components, such as an antibody, an antibody fragment, an analog or derivative thereof. Molecules incorporating combinations of the aforementioned components (e.g., radionuclide-chelate-ligand, radionuclide-chelate-anti-ligand, antibody-chelate-radionuclide, antibody-ligand-drug, antibody-anti-ligand-drug, antibody-ligand-chelate-radionuclide, antibody-anti-ligand-chelate-radionuclide and the like) are useful in the practice of the present invention. The improved biodistribution properties of DBM-containing complexes or conjugates of the present invention are imparted by covalent binding, non-covalent complexing or otherwise associating a small molecule component (including one or more small molecules) to or with a DBM component exhibiting such improved characteristics.

One DBM property that facilitates the favorable biodistribution thereof is size. In one embodiment of the present invention, one or more small molecules are bound to or associated with a large (e.g., polymeric) DBM, wherein the DBM masks the small molecule such that the biodistribution of the small molecule substantially corresponds to that of the DBM, while maintaining any binding properties of the small molecule(s) necessary for proper targeting. More specifically, the biodistribution properties of the small molecule are blocked or overridden by those of the DBM. For instance, sites on the small molecule recognized, for example, by liver cells are rendered sterically unavailable for liver cell binding or otherwise fail to be recognized by liver cells as a result of the DBM structure or DBM-small molecule(s) conjugate or complex configuration.

Another benefit imparted by size is the ability to bind a plurality of active agents. Increasing the concentration of active agent at the target enhances the efficacy of the active agent and the protocol in which it is used. Polymeric and other intermediate or high molecular weight DBMs, having a plurality of available functional groups for direct or indirect active agent binding or exhibiting the capability of derivitization to acquire such functional groups, are exemplary multiple active agent binding DBMs. Preferred DBMs having this characteristic, which also impart renal clearance properties to associated small molecules, include dextran, carboxymethyl cellulose, hydroxypropylmethacrylamide polymers (HPMA), carboxymethyl dextrans, polyethyleneglycol (PEG), polyaspartate, polyglutamate and succinylated polylysine. A more preferred DBM incorporates dextran, such preferred molecules including biotin-dextran, lysine fixable (BDLF) and other aminodextran-based molecules. Preferred DBM-small molecule conjugates useful in the practice of the present invention are directly or indirectly (i.e., through a chelate) radiolabeled biotin-dextran, somatostatin- or somatostatin derivative-dextran as well as antibody- or antibody fragment-dextran.

Another property of DBMs that influences the biodistribution thereof is charge. Consequently, conjugates or complexes of the present invention exhibiting improved biodistribution characteristics include small molecule(s) bound to, complexed with or associated with a highly polar molecule having desirable renal clearance biodistribution characteristics. This desirable property is imparted to the small molecule as a consequence of conjugation or complexation of the small molecule to the DBM. Preferred DBM-small molecule conjugates of this aspect of the present invention include diethylene triamine penta-acetic acid (DTPA) or derivatives or analogs thereof bound to a targeting moiety, such as an antibody, antibody fragment, oligonucleotide or other small proteinaceous molecule, a ligand, an anti-ligand, a stable chelate such as an $N_2S_2$ mercaptodiamide molecule, or a combination thereof. More preferred DBM-small molecule conjugates or complexes of this aspect of the present invention are radiolabeled DTPA derivative-antibody or -antibody fragment, DTPA derivative-somatostatin or -somatostatin derivative and DTPA derivative-biotin.

DBM-small molecule complexes or conjugates of the present invention are useful in the delivery of a variety of therapeutic and diagnostic active agents to target cell populations using targeted, direct labeled protocols (e.g., administration of targeting moiety-DBM-active agent or active agent-targeting moiety-DBM conjugate or complex) and pretargeting approaches (e.g., administration of targeting moiety-anti-ligand followed by administration of ligand-DBM-active agent or active agent-ligand-DBM conjugate or complex). Such targeted, direct-labeled diagnostic and therapeutic protocols and diagnostic and therapeutic pretargeting protocols are also contemplated by the present invention. Drugs, diagnostic radionuclides and therapeutic radionuclides are preferred active agents for delivery in accordance with the present invention.

An additional aspect of the present invention provides renal excretion of active agent-containing conjugate or complex metabolites. More specifically, the present invention provides chelate-DBM-proteinaceous targeting moiety conjugates or complexes which are metabolized to form amino acid adducts of the chelate-DBM portion of the conjugate or complex. These adducts are excreted by a renal pathway as a result of the DBM component thereof.

DETAILED DESCRIPTION OF PREFERRED EMBODIMENTS

Figure 1A:
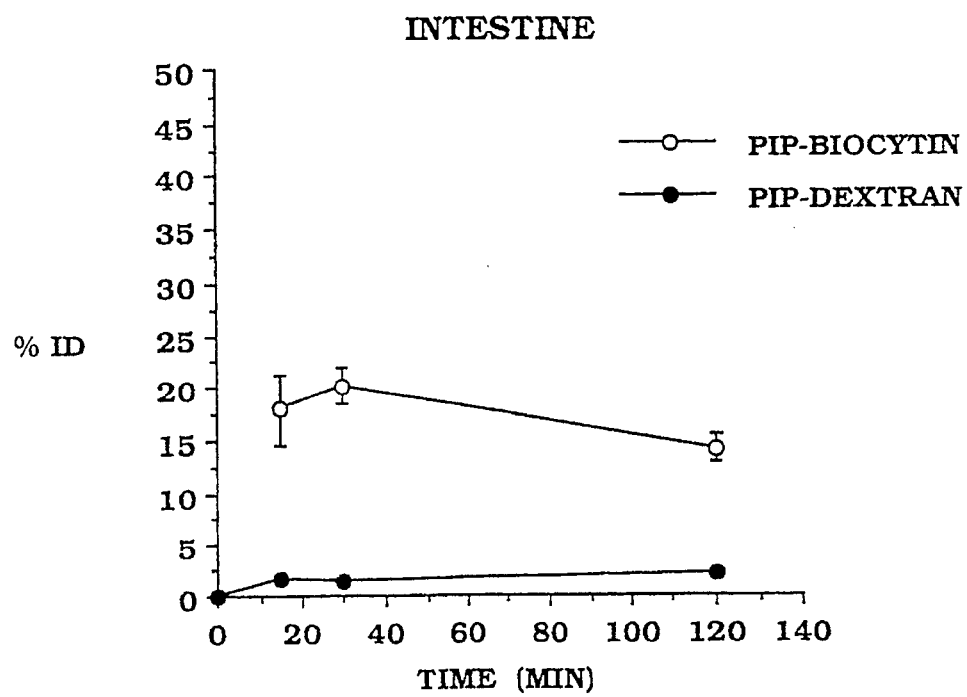
FIG. 1A depicts the percent injected dose of radiolabeled PIP-biocytin and biotin-dextran in the intestine over time.
Figure 1B:
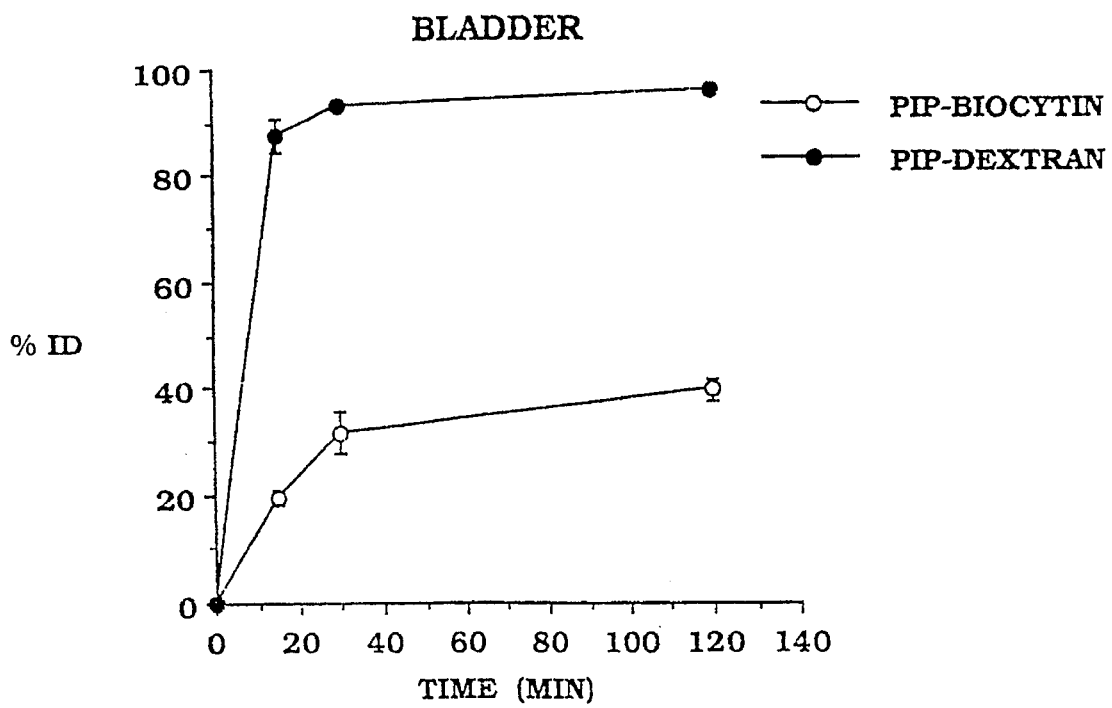
FIG. 1B depicts the percent injected dose of radiolabeled PIP-biocytin and biotin-dextran in the bladder over time.
Figure 1C:
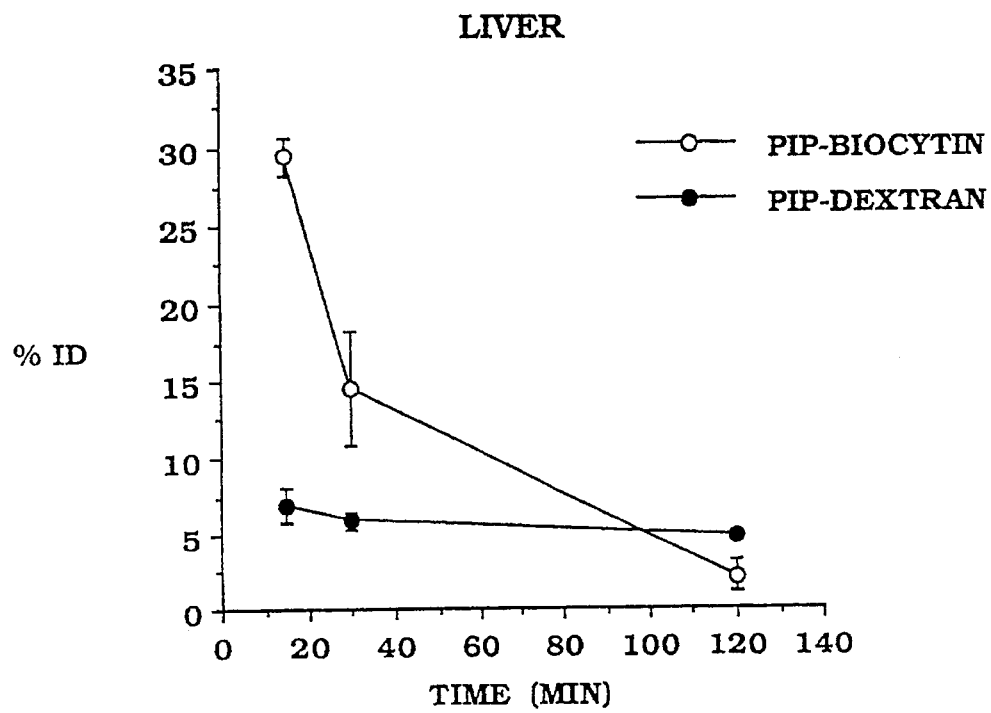
FIG. 1C depicts the percent injected dose of radiolabeled PIP-biocytin and biotin-dextran in the liver over time.
Figure 1D:
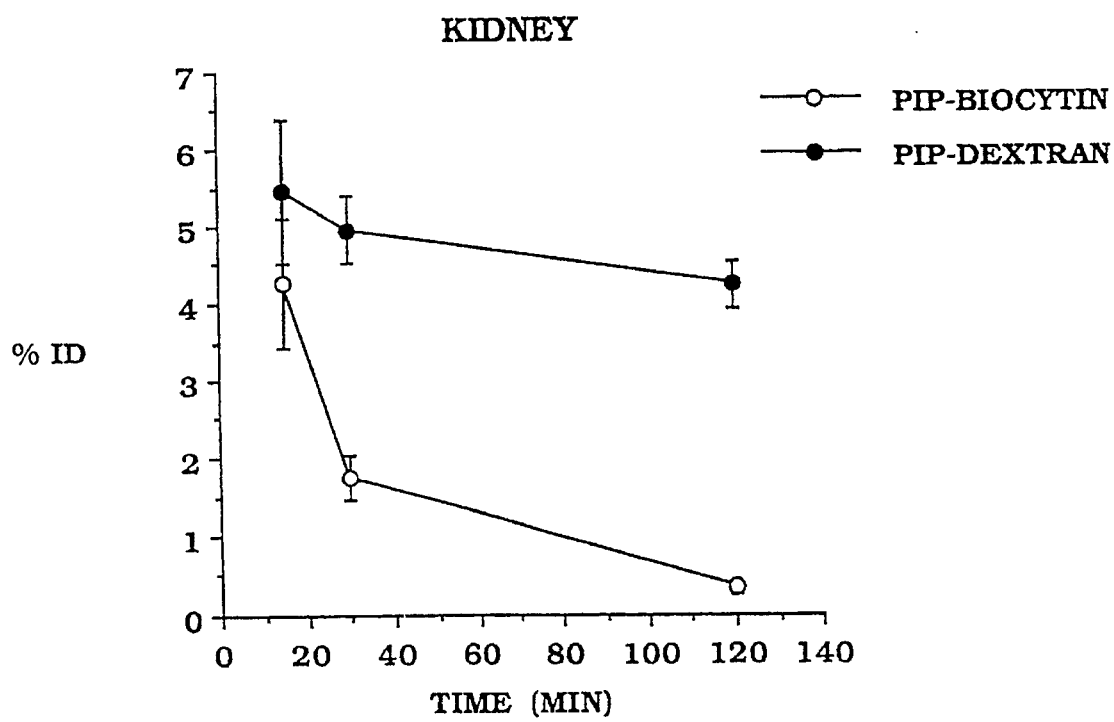
FIG. 1D depicts the percent injected dose of radiolabeled PIP-biocytin and biotin-dextran in the kidney over time.
Figure 1E:
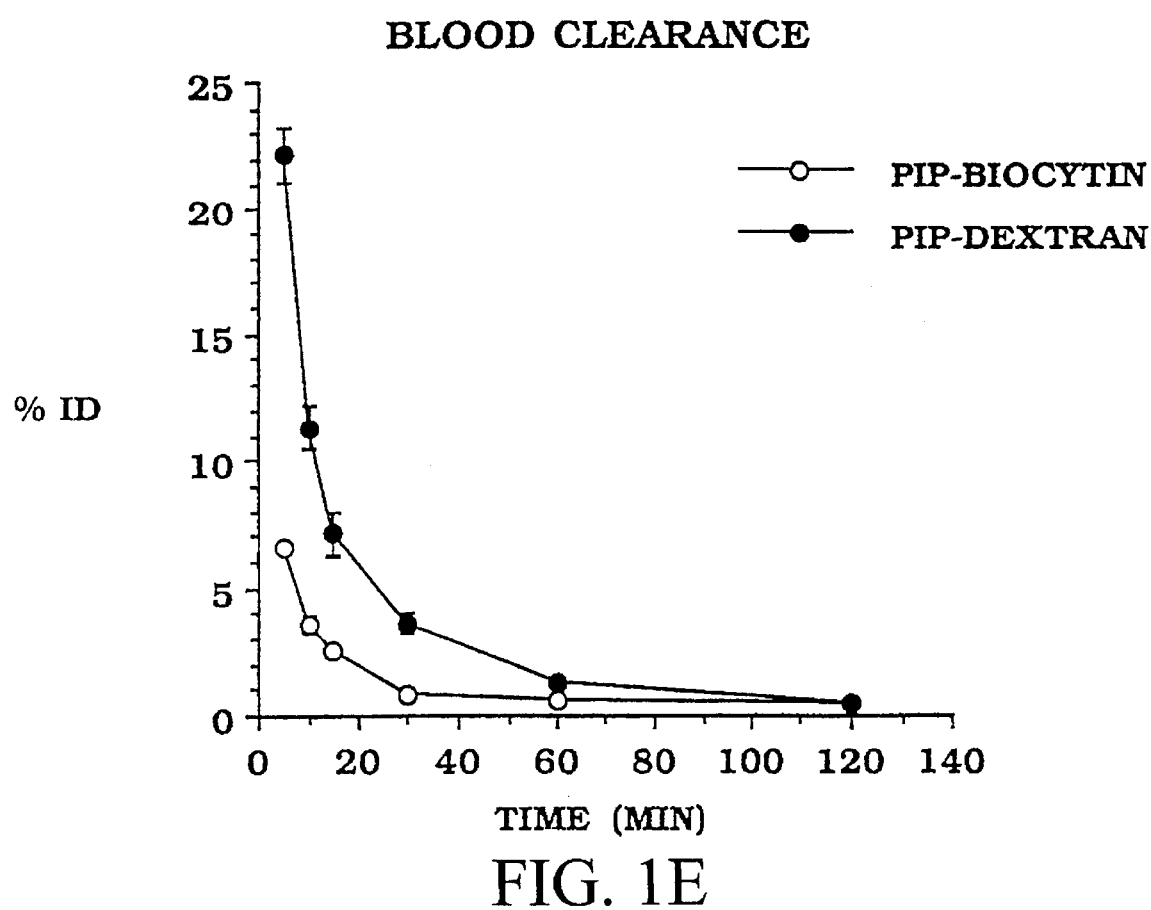
FIG. 1E depicts the percent injected dose of radiolabeled PIP-biocytin and biotin-dextran in the blood over time.

Prior to describing preferred embodiments of the present invention, definitions of terms thought to be useful in the understanding the invention are set forth.

Chelate: Bifunctional chelates that are capable of (i) coordinately binding a metal or radiometal and (ii) covalently attaching to a DBM, targeting moiety, ligand or anti-ligand. Preferred chelates are $N_xS_y$ chelates.

$N_xS_y$ Chelates: Bifunctional chelators that are capable of (i) coordinately binding a metal or radiometal and (ii) covalently attaching to a DBM, targeting moiety, ligand or anti-ligand. Particularly preferred $N_xS_y$ chelates have $N_2S_2$ and $N_3S$ cores. Exemplary $N_xS_y$ chelates are described in Fritzberg et al., *Proc. Natl. Acad. Sci. USA* 85:4024–29, 1988; in Weber et al., *Bioconj. Chem.* 1:431–37, 1990; and in the references cited therein, for instance.

Directed Biodistribution Molecule (DBM): A moiety that is excreted through a renal pathway when administered to a mammalian recipient and that is capable of covalently or non-covalently binding to one or more antibodies or antibody fragments as well as drugs, peptides, chelates, ligands, anti-ligands or other small molecules and imposing a renal route of excretion upon the associated molecule(s). DBMs include polar molecules having a molecular weight ranging from about 3 kD to about 70 kD) or highly polar or ionic moieties having a molecular weight below about 2 kD.

Targeting moiety: A molecule that binds to a defined population of cells. The targeting moiety may bind a receptor, an oligonucleotide, an enzymatic substrate, an antigenic determinant, or other binding site present on or in the target cell population. Antibodies and peptides are used throughout the specification as prototypical examples of targeting moieties. Tumor is used as a prototypical example of a target in describing the present invention.

Ligand/anti-ligand pair: A complementary/anti-complementary set of molecules that demonstrate specific binding, generally of relatively high affinity. Exemplary ligand/anti-ligand pairs include hapten/antibody, lectin/carbohydrate, ligand/receptor, and biotin/avidin or biotin/streptavidin. Biotin/streptavidin is used throughout the specification as a prototypical example of a ligand/anti-ligand pair.

Anti-ligand: A moiety demonstrating high affinity, and preferably, multivalent binding of the complementary ligand. Preferably, the anti-ligand is large enough to avoid rapid renal clearance, and contains sufficient multivalency to accomplish crosslinking and aggregation of targeting moiety-ligand conjugates. Univalent anti-ligands are also contemplated by the present invention. Streptavidin is used as a prototypical anti-ligand.

Streptavidin: This term includes streptavidin and avidin as well as derivatives and analogs thereof that are capable of high affinity, multivalent or univalent binding of biotin.

Ligand: A relatively small, soluble molecule that exhibits rapid serum, blood and/or whole body clearance when administered intravenously in a mammal. Biotin is used as the prototypical ligand.

Active Agent: A diagnostic or therapeutic agent, including radionuclides, drugs, and the like. Radionuclide therapeutic agents are used as prototypical active agents.

Small Molecule: A molecule having a molecular weight below about 2 kD, including one or more of the following components: a catabolite derived from targeting moieties, such as an antibody or an antibody fragment; an oligonucleotide; a peptide; a drug, a ligand, an anti-ligand, a chelate or the like. Small molecules of the present invention preferably include a diagnostic or a therapeutic active agent when administered to a mammal. For the purposes of this description, chelate, antibody metabolite, somatostatin (and derivatives thereof), biotin, radiolabeled antibody metabolite, radiolabeled somatostatin (and somatostatin derivatives) and radiolabeled biotin are prototypical small molecules useful in the practice of the present invention.

Complex: A multi-component molecule incorporating two or more functionally different moieties that are not covalently bound. Complexes of the present invention are associated through non-covalent binding, such as ionic bonding, van der Waals force-based coupling, hydrogen bonding and the like. Exemplary complexes of the present invention incorporate one or more small molecules and a DBM. Other complexes additionally include an active agent or an antibody or an antibody fragment targeting moiety.

Conjugate: A multi-component molecule incorporating two or more functionally different moieties that are covalently bound. Exemplary conjugates of the present invention incorporate one or more small molecules and a DBM. Other conjugates additionally include an active agent or an antibody or an antibody fragment targeting moiety. For the purposes of the following description, the term "conjugate" shall include "complexes."

Targeted, Direct Labeled Protocol: Administration of a conjugate or a complex containing a targeting moiety and an active agent, such that the targeting moiety directs the localization of the conjugate or complex to a target cell population, and the active agent exerts a diagnostic or a therapeutic effect. DBMs of the present invention are covalently or non-covalently bound to either or both of these components and direct the biodistribution of the conjugates/complexes or active agent-containing metabolites thereof to renal excretion.

Pretargeting: Target site localization of a targeting moiety that is conjugated with one member of a ligand/anti-ligand pair; after a time period sufficient for optimal target-to-non-target accumulation of this targeting moiety conjugate, active agent conjugated to the opposite member of the ligand/anti-ligand pair is administered and is bound (directly or indirectly) to the targeting moiety conjugate at the target site. Three-step pretargeting (i.e., administration of targeting moiety-ligand; anti-ligand administration; and administration of active agent-ligand) and other related methods described herein are also encompassed.

The present invention is directed to DBM-small molecule conjugates characterized by renal excretion. Preferably, the conjugates of the present invention deliver a diagnostic or therapeutic agent to a target cell population determined by the binding specificity of a targeting moiety, ligand or anti-ligand conjugate component. Consequently, preferred embodiments of the invention can be represented as follows:

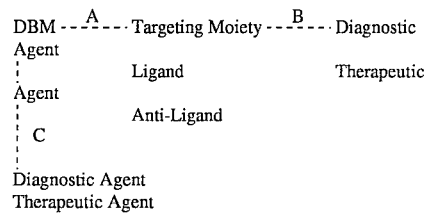

where either bond "B" or bond "C" links the active agent to the conjugate.

DBM-small molecule conjugates of the present invention are useful in a variety of therapeutic and diagnostic protocols. Preferred protocols may be generally characterized as targeted, direct-labeled and pretargeting approaches. Typically, a targeted, direct-labeled approach involves administering to a mammalian recipient an agent selected from those schematically represented below, with molecules of the first two structures preferred.

Targeting Moiety ------ DBM ------ Active Agent or

Active Agent ------ Targeting Moiety ------ DBM or

Targeting Moiety ------ Active Agent ------ DBM

In this manner, active agent is delivered to the target cell population to which the targeting moiety localizes, while non-targeted conjugate as well as the metabolic byproducts thereof bearing the active agent are excreted, with the excretion proceeding primarily through the renal pathway. Undesirable hepatobiliary excretion of active agent are decreased in the practice of the present invention.

Pretargeting encompasses two protocols, termed the three-step and the two-step. In the three-step protocol shown schematically below, targeting moiety-ligand is administered and permitted to localize to target.

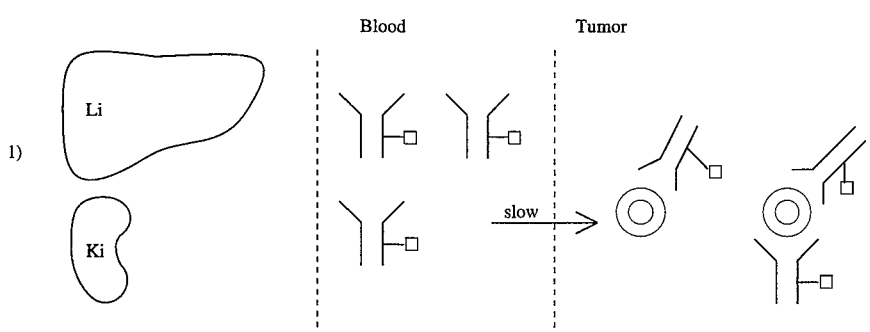

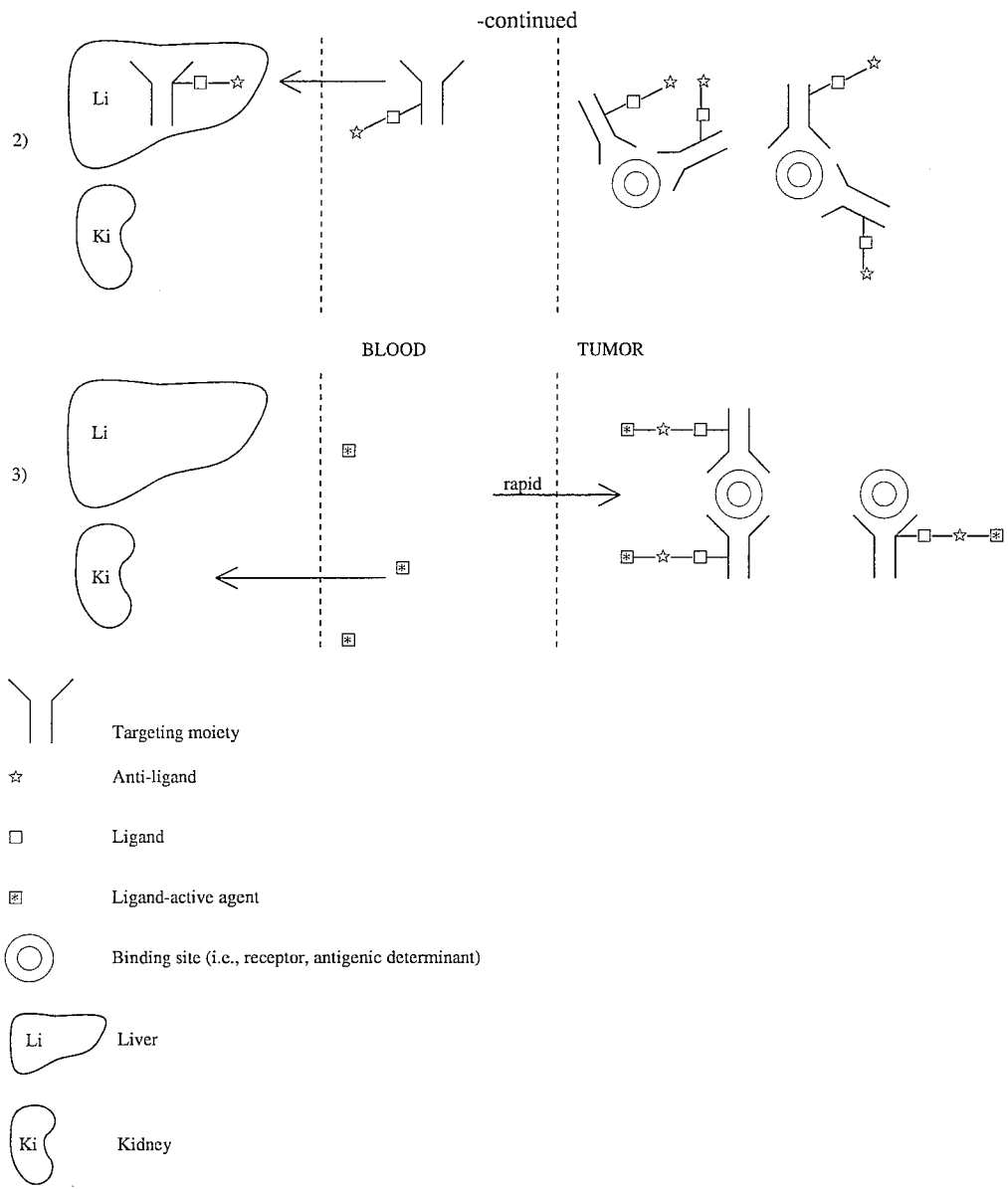

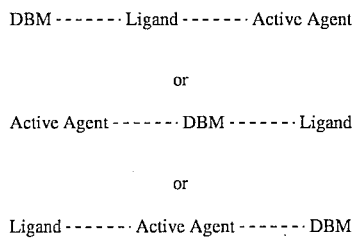

Anti-ligand is then administered to act as a clearing agent and facilitate and direct the excretion of circulating targeting moiety-ligand. The anti-ligand also binds to target-associated targeting moiety-ligand. Next, a conjugate of the present invention is administered, preferably selected from the following schematic structures:

DBM ------ Ligand ------ Active Agent or

Active Agent ------ DBM ------ Ligand or

Ligand ------ Active Agent ------ DBM

The former two structures are preferred in the practice of the present invention. The DBM/ligand/active agent conjugate either binds to target-associated targeting moiety-ligand-anti-ligand or is preferably rapidly excreted, with the excretion proceeding primarily through the renal pathway. Consequently, the target-non-target ratio of active agent is improved, and undesirable hepatobiliary excretion and intestinal uptake of the active agent are substantially decreased.

Two-step pretargeting involves administration of targeting moiety-anti-ligand. After permitting the administered agent to localize to target, a conjugate of the present invention is administered, preferably selected from the aforementioned ligand-DBM-active agent or active agent-ligand-DBM conjugates of the present invention Preferably, as a "step 1.5," a clearing agent is administered to remove circulating targeting moiety-anti-ligand without binding to target-associated targeting moiety-anti-ligand. In this manner, the target-non-target ratio of the active agent is increased, and undesirable hepatobiliary excretion and intestinal uptake of the active agent are substantially decreased.

The "targeting moiety" of the present invention binds to a defined target cell population, such as tumor cells. Preferred targeting moieties useful in this regard include antibody and antibody fragments, peptides, and hormones.

Proteins corresponding to known cell surface receptors (including low density lipoproteins, transferrin and insulin), melanocyte stimulating hormone, somatostatin, somatostatin derivatives, such as octreotide and MK-678 (Merck), fibrinolytic enzymes, HER2 ligand, and biological response modifiers (including interleukin, interferon, erythropoietin and colony-stimulating factor) are also preferred targeting moieties. Oligonucleotides, e.g., antisense oligonucleotides that are complementary to portions of target cellular nucleic acids (DNA or RNA), are also useful as targeting moieties in the practice of the present invention. Oligonucleotides binding to cell surfaces are also useful. Analogs of the above-listed targeting moieties that retain the capacity to bind to a defined target cell population may also be used within the claimed invention. In addition, synthetic targeting moieties having such binding specificity may be designed.

Functional equivalents of the aforementioned molecules are also useful as targeting moieties of the present invention. One targeting moiety functional equivalent is a "mimetic" compound, an organic chemical construct designed to mimic the proper configuration and/or orientation for targeting moiety-target cell binding. Another targeting moiety functional equivalent is a short polypeptide designated as a "minimal" polypeptide, constructed using computer-assisted molecular modeling and mutants having altered binding affinity, which minimal polypeptides exhibit the binding affinity of the larger targeting moiety.

Preferred targeting moieties of the present invention are antibodies (polyclonal or monoclonal), peptides, oligonucleotides or the like. Polyclonal antibodies useful in the practice of the present invention are polyclonal (Vial and Callahan, *Univ. Mich. Med. Bull.*, 20: 284–6, 1956), affinity-purified polyclonal or fragments thereof (Chao et al., *Res. Comm. in Chem. Path. & Pharm.*, 9:749–61, 1974).

Monoclonal antibodies useful in the practice of the present invention include whole antibody and fragments thereof. Such monoclonal antibodies and fragments are producible in accordance with conventional techniques, such as hybridoma synthesis, recombinant DNA techniques and protein synthesis. Useful monoclonal antibodies and fragments may be derived from any species (including humans) or may be formed as chimeric proteins which employ sequences from more than one species. See, generally, Kohler and Milstein, *Nature*, 256: 495–97, 1975; *Eur. J. Immunol.*, 6:511–19, 1976.

Human monoclonal antibodies or "humanized" murine antibody are also useful as targeting moieties in accordance with the present invention. For example, murine monoclonal antibody may be "humanized" by genetically recombining the nucleotide sequence encoding the murine Fv region (i.e., containing the antigen binding sites) or the complementarity determining regions thereof with the nucleotide sequence encoding a human constant domain region and an Fc region, e.g., in a manner similar to that disclosed in European Patent Application No. 0,411,893 A2. Humanized targeting moieties are recognized to decrease the immunoreactivity of the antibody or polypeptide in the host recipient, permitting an increase in the half-life and a reduction in the possibility of adverse immune reactions. Retention of murine CDR regions and framework regions is preferably undertaken when "humanizing" antibodies to be used in the practice of the present invention.

Types of active agents (diagnostic or therapeutic) useful herein include drugs and radionuclides. Preferred drugs suitable for use herein include conventional chemotherapeutics, such as vinblastine, doxorubicin, bleomycin, methotrexate, 5-fluorouracil, 6-thioguanine, cytarabine, cyclophosphamide and cis-platinum, as well as other conventional chemotherapeutics as described in *Cancer: Principles and Practice of Oncology*, 2d ed., V. T. DeVita, Jr., S. Hellman, S. A. Rosenberg, J. B. Lippincott Co., Philadelphia, Pa., 1985, Chapter 14. A preferred drug within the present invention is a trichothecene, because a plurality of drug molecules are deliverable to the target for each targeting moiety employed.

Experimental drugs, such as mercaptopurine, N-methylformamide, 2-amino-1,3,4-thiadiazole, melphalan, hexamethylmelamine, gallium nitrate, 3% thymidine, dichloromethotrexate, mitoguazone, suramin, bromodeoxyuridine, iododeoxyuridine, semustine, 1-(2-chloroethyl)-3-(2,6-dioxo-3-piperidyl)-1-nitrosourea, N,N'-hexamethylene-bisacetamide, azacitidine, dibromodulcitol, Erwinia asparaginase, ifosfamide, 2-mercaptoethane sulfonate, teniposide, taxol, 3-deazauridine, soluble Baker's antifol, homoharringtonine, cyclocytidine, acivicin, ICRF-187, spiromustine, levamisole, chlorozotocin, aziridinyl benzoquinone, spirogermanium, aclarubicin, pentostatin, PALA, carboplatin, amsacrine, caracemide, iproplatin, misonidazole, dihydro-5-azacytidine, 4'-deoxydoxorubicin, menogaril, triciribine phosphate, fazarabine, tiazofurin, teroxirone, ethiofos, N-(2-hydroxyethyl)-2-nitro-1H-imidazole-1-acetamide, mitoxantrone, acodazole, amonafide, fludarabine phosphate, pibenzimol, didemnin B, merbarone, dihydrolenperone, flavone-8-acetic acid, oxantrazole, ipomeanol, trimetrexate, deoxyspergualin, echinomycin, and dideoxycytidine (see *NCI Investigational Drugs, Pharmaceutical Data* 1987, NIH Publication No. 88-2141, Revised November 1987) are also preferred.

Radionuclides useful within the present invention include gamma-emitters, positron-emitters, Auger electron-emitters, X-ray emitters and fluorescence-emitters, with beta- or alpha-emitters preferred for therapeutic use. Radionuclides are well-known in the art and include $^{123}I$, $^{125}I$, $^{130}I$, $^{131}I$, $^{133}I$, $^{135}I$, $^{47}Sc$, $^{72}As$, $^{72}Se$, $^{90}Y$, $^{88}Y$, $^{97}Ru$, $^{100}Pd$, $^{101m}Rh$, $^{119}Sb$, $^{128}Ba$, $^{197}Hg$, $^{211}At$, $^{212}Bi$, $^{153}Sm$, $^{169}Eu$, $^{212}Pb$, $^{109}Pd$, $^{111}In$, $^{67}Ga$, $^{68}Ga$, $^{67}Cu$, $^{75}Br$, $^{76}Br$, $^{77}Br$, $^{99m}Tc$, $^{11}C$, $^{13}N$, $^{15}O$ and $^{18}F$. Preferred therapeutic radionuclides include $^{188}Re$, $^{186}Re$, $^{203}Pb$, $^{212}Pb$, $^{212}Bi$, $^{109}Pd$, $^{64}Cu$, $^{67}Cu$, $^{90}Y$, $^{125}I$, $^{131}I$, $^{77}Br$, $^{211}At$, $^{97}Ru$, $^{105}Rh$, $^{198}Au$ and $^{199}Au$ or $^{177}Lu$.

The radionuclides useful in the practice of the present invention are covalently bound to or are complexed with a chelate capable of stably associating with the radionuclide and with the DBM or other conjugate component. In this manner, the radionuclide active agent is directly or indirectly associated with the DBM which directs the biodistribution of the radionuclide. Exemplary chelates are $N_xS_y$ chelates as previously discussed; para-iodo-phenyl (PIP)-based chelates described, for example, in Wilbur, et al., *J. Nucl. Med.*, 30: 216–226, 1989; and the like.

Radionuclide complexation is generally conducted in accordance with standard techniques therefor (e.g., preformed or post-formed approaches). Also, chelate binding to DBMs, ligands, anti-ligands or other conjugate components is accomplished by standard coupling procedures for formation of amides, esters, ethers and the like. Chelate-DBM conjugation is accomplished through an active ester chelate derivative, wherein exemplary active esters are N-hydroxysuccinimide, tetrafluorophenyl and the like). Michael addition reactions employing, for example, a maleimide group, can also be used for this purpose.

One aspect of the present invention is a conjugation technique characterized by minimized labeling time and defined chemistry for radiolabel attachment. The inventive synthesis is schematically shown below.

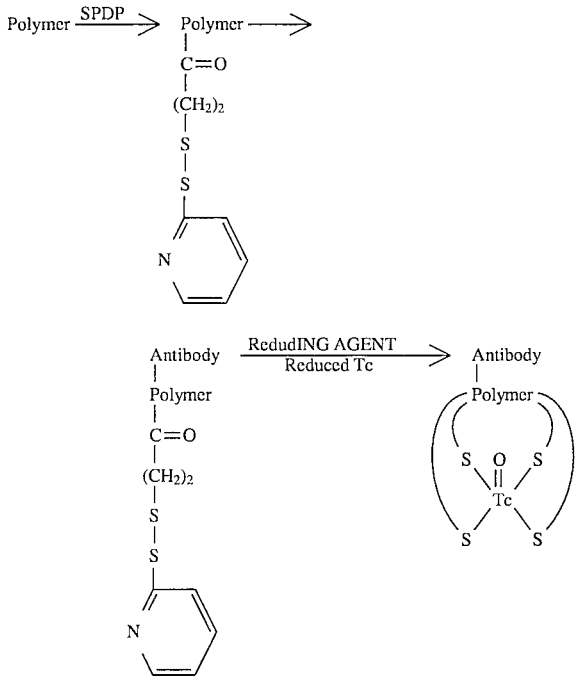

This post-formed approach of the present invention involves derivitization of a polymeric species (e.g., dextran, polylysine or the like) with a thiolating agent to incorporate thiol functional groups into the polymer structure. For example, exemplary thiolating agents include N-succinimidyl 3-(2-pyridyldithio) propionate (SPDP), iminothiolane, N-succinimidyl-S-acetylthioacetate (SATA), dimercaptosuccinyl derivatives and the like. The thiolating agent-derivitized polymer is then covalently attached to antibody, another targeting moiety, ligand, anti-ligand or the like. For example, antibody is conjugated to the derivitized polymers using a water soluble carbodiimide. Any other convenient conjugation procedure can be employed at this stage. Under reducing conditions, the thiol moieties generated by the SPDP or similar derivitization of the polymer react with a reduced radionuclide, such as technetium, rhenium or the like, resulting in rapid chelation of the radionuclide. This technique is addressed in Example I(C) hereof. This synthesis offers the following advantages:

Protein (proteinaceous targeting moiety, ligand or anti-ligand) integrity is maintained, because the radionuclide labeling does not occur directly thereon;

Reactive thiols can be generated on the polymeric DBM only;

Chelation is likely to proceed through an $S_4$ complex with no participation from functionalities present on the targeting moiety (especially proteinaceous targeting moieties), ligand or anti-ligand;

The tentacle-like configuration of the reactive thiols located on the polymer DBM facilitate proper orientation and maximum stability for the resultant radionuclide-chelate complex; and Metabolites of the product conjugate containing radionuclide are preferably excreted via the desirable renal pathway.

An alternative "tentacle chelate" formation process involves thiol functional group generation using a thiolating agent in the presence of reduced radionuclide. A reducing agent capable of concurrent reduction of radionuclide and thiolating agent in the presence of protein is required to carry out this alternative method. For technetium radionuclide and SPDP thiolating agent, useful reducing agents include. stannous ion, dithionite, sulfites, cuprous ion, chromous ion, phosphines and the like. Other examples of chelate-containing conjugates of the present invention and syntheses therefor are set forth below.

Ligands suitable for use within the present invention include biotin, haptens, lectins, epitopes and analogs and derivatives thereof. Useful complementary anti-ligands include avidin (for biotin), carbohydrates (for lectins) and antibody, fragments or analogs thereof, including mimetics (for haptens and epitopes). Preferred ligand-anti-ligands binding pairs associate with each other at an affinity of at least about $k_D \geq 10^9 M$.

DBMs of the present invention exhibit renal excretion as well as the ability to direct the excretion of targeting moieties or small molecules bound thereto to renal excretion, while maintaining binding site recognition and binding by the targeting moiety. In addition, preferred DBMs exhibit one or more of the following characteristics: hydrophilicity, polar structure, neutral or anionic charge, non-toxicity to mammalian recipients, a lack of molecular units recognizable by organ receptors, stability in serum, tumor bioavailability and the like. More preferred DBMs are so specifically excreted by the kidneys that when small molecules are bound to the DBM, the conjugated DBM and active agent-containing metabolites thereof are still specifically excreted by the kidneys.

One type of DBM molecule, a large (i.e., of intermediate to high molecular weight ranging from about 5,000 Dal. to about 70,000 Dal.), preferably polymeric (i.e., incorporating from about 30 to about 500 monomeric units) DBM, "masks" the biodistribution properties of the targeting moiety or small molecule conjugate components and prevents liver cell recognition of such moieties necessary for hepatic uptake and biliary excretion thereof. These DBMs of the present invention also preferably exhibit polar structure. Exemplary of such DBMs are dextran; dextran derivatives including carboxymethyl dextran, aminodextran, 3-mercapto-2-hydroxypropyl dextran and the like; hyaluronic acid, inulin, carboxymethyl cellulose; hydroxy-propylmethacrylamide (HPMA) polymers; succinylated polylysine; polyaspartate; polyglutamate; polyethyleneglycol (PEG); and the like.

The disposition characteristics of macromolecules have been investigated. See, for example, Takakura, et al., *Pharm. Res.*, 7:339, 1990. For example, dextrans having a molecular radii of less than 20 angstroms have been reported to cross the glomerulus without measurable restriction by Hurwitz, et al., *Eur. J. Cancer*, 14:1213, 1978. Antibody-drug binding using dextran has been documented. See, Hurwitz et al. cited above. Also, the water solubility of polymeric macromolecules has been exploited to provide simplified protocols for the preparation of soluble, multivalent macromolecular conjugates. See U.S. Pat. No. 5,026,785.

For use in the present invention, dextran DBMs preferably range between about 5 and about 15 kD in size, although larger moieties may also be used. These dextran DBMS are capable of binding multiple and varied small molecules and larger targeting moieties such as antibodies and antibody fragments. More specifically, dextran DBMS useful in pretargeting applications of the present invention may bind one or more ligands or anti-ligands as well as one or more active agents. That is, dextran DBMs of the present invention useful in pretargeting applications thereof may bind, for example, from about 1 to about 3 biotin molecules as well as from about 1 to about 5 chelating groups. For targeted, direct labeled methods of the present invention, DBMs are bound to one or more targeting moieties (e.g., antibodies) and one or more active agents (e.g., chelating agents having a radionuclide complexed therein).

When larger (from about 40 to about 70 kD) polymers are employed as DBMs in accordance with the present invention, the rate of clearance of the conjugate from a recipient is slowed, but the renal pathway for excretion is maintained. In this manner, small molecules or larger targeting moieties bound to the DBM exhibit increased bioavailability as a result of the increased circulation time thereof. Such bound molecules remain directed to renal excretion, however.

Exemplary dextran DBM-containing conjugates of the present invention are dextran-biotin conjugates. Chelate-biotin-dextran conjugates of the present invention are formed, for example, from oxidized dextran by conjugating biocytin hydrazide thereto followed by reaction with a chelate active ester, such as a N-hydroxy succinimidyl ester, a tetrafluorophenyl ester and the like. Alternatively, chelate-biotin-dextran can be formed by reacting dextran hydrazide with the carboxy terminus of a chelate-biocytin conjugate. Preferably, the carboxy terminus has been derivitized to form an active ester, such as an N-hydroxysuccinimidyl ester or the like. Examples of these reaction schemes are discussed in Examples II–IV hereof.

A pre-formed Re-labeling approach useful in the practice of the present invention involves rhenium labeling of biotin-dextran conjugate through acylation with a rhenium complex active ester, such as a tetrafluorophenyl ester as discussed in Example IV(B). A post-formed Re-labeling approach may also be used in accordance with the present invention. As set forth in Example IV(A), the chelating group is conjugated to dextran-biotin conjugate prior to Re chelate labeling in the presence of SnCl$_2$ and citric acid.

The molar ratio of biotin/dextran in biotin-dextran conjugates of the present invention can be altered by a practitioner in the art to form molecules having different structures by modifying the offering ratio of the ligand with respect to the polymer. For example, an increased offering ratio of biocytin hydrazide to dextran results in conjugates characterized by an increased number of bound biotin molecules. Tumor targeting can therefore be optimized with respect to the parameter of molar ratio.

Biotin-dextran, lysine fixable (BDLF, available from Sigma Chemical Company, St. Louis, Mo.) is a preferred DBM-ligand of the present invention. BDLF is characterizable as follows:

biotin and lysine carboxyl groups are attached by amide linkages to amino groups of aminodextran;

biotin attached to dextran through an amine; and 2 moles biotin/dextran (10,000 dalton molecular weight) or 20 moles biotin/dextran (70,000 dalton molecular weight). Based upon available information, the structure of BDLF (10,000 dalton) is believed to be the following:

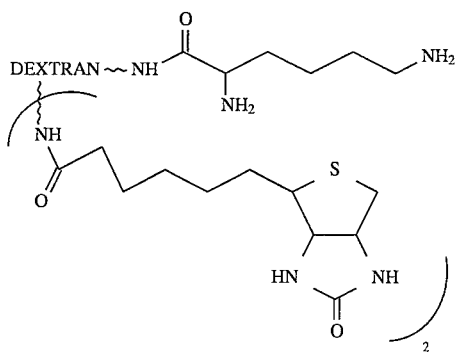

Iodine labeling of BDLF is conducted through acylation with a chelate-active ester, such as N-hydroxysuccinimidyl p-iodobenzoate, as discussed in Example III below. Additional procedures for preparing BDLF-containing conjugates of the present invention are discussed in Example IV below. The BDLF structure depicted above accommodates the binding of a small molecule or active agent, e.g., at the lysine epsilon amino group. Two small molecules or active agents, e.g., radionuclide chelates, may be bound to a derivitized BDLF, an example of such a dual derivitization being shown below:

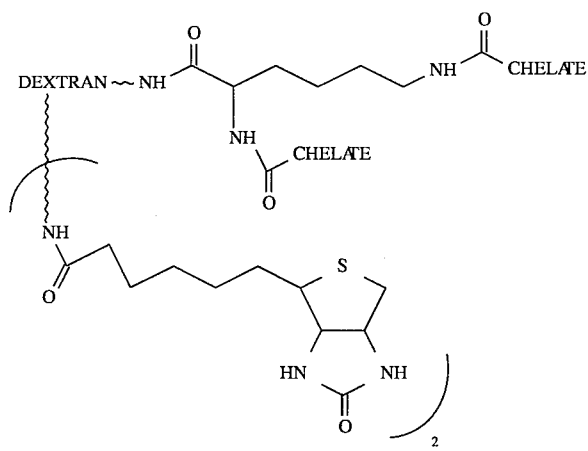

A chelate-dextran-antibody conjugate can be prepared from dextran hydrazide, for example, by reaction of the polymer with a derivitized chelate having an aldehyde functional group and with an oxidized antibody or an antibody-glutaraldehyde conjugate. In addition, antibody-chelate-dextran moieties of the present invention are preparable from carboxymethyl dextran by reacting the polymer with a chelate bearing a first functional group reactive with the modified dextran (e.g., an alcohol to form an ester with the carboxyl moiety of carboxymethyl dextran, an amine to form an amide with such carboxyl moieties or the like) and a second functional group reactive with an antibody or a derivitized antibody (e.g., a maleimide group to react with a free sulfhydryl moiety on the antibody, an aldehyde group to react with an amine moiety located on the antibody, a protected carboxyl group to be deprotected and activated to react with an antibody amino group or the like). Exemplification of these protocols is shown in Example V hereof.

Chelate-somatostatin derivative (e.g., octreotide)-dextran conjugates are prepared from carboxymethyl dextran, for example, by conjugation of D-Phe-octreotide to the polymer at the amino terminus of the peptide, while the chelate is bound through an amino group to the peptide at the carboxy terminus. The octreotide-polymer bond is formed, for example, by reaction of the peptide terminal amino group with carbodiimide or a pre-activated polymer carboxyl (e.g., an active ester). Also, the chelate-peptide bond is formed, for example, by reaction of the peptide terminal carboxyl group and a chelate amino group, using either carbodiimide or active ester coupling chemistry.

Alternatively, dextran hydrazide is conjugated to the carboxy terminus of D-Phe-octreotide, and a chelate active ester is linked to the amino terminus. Exemplary active esters employable for this purpose are N-hydroxysuccinimide, tetrafluorophenyl ester and the like. Also, the chelate may be bound at the carboxy terminus of the peptide (through a chelate functional group, such as an amino group or the like), and the chelate-peptide is then conjugated to oxidized dextran. Moreover, the chelate-peptide bond may be formed, for example, by reaction of the peptide terminal amino group with an aldehyde functional group of oxidized dextran. In addition, reaction of aminodextran with the carboxy terminus of the peptide can be employed following reaction of a chelate active ester at the peptide amino terminus. These reaction schemes are the subject of Example VI hereof.

As in all three component embodiments of the present invention, dextran/octreotide/chelate conjugates are amenable to three configurations as follows:

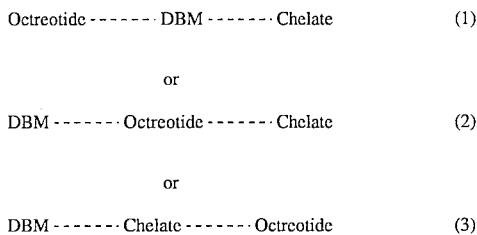

In configuration (1), modification of octreotide is minimized, because the somatostatin analog is required to bind to the DBM only. In configuration (2), chelate-octreotide-glucose is retained upon conjugate metabolism, thereby preserving the targeting moiety and active agent as a single entity.

In addition, chelating agents can be bound to dextran DBMs characterized by short term serum stable linkages disposed between monomeric, dimeric, trimeric or other convenient unit thereof. Such conjugates are also preferably large (exhibiting a molecular weight ranging from about 40 to about 70 kD) These conjugates of the present invention are used to enhance the absolute amount of an active agent (e.g., radionuclide, drug, anti-tumor agent or the like) or other small molecule (e.g., ligand, anti-ligand, peptide or the like) or larger targeting moiety (e.g., antibody or antibody fragment) localizing to target sites. One advantage of such polymer DBMs is that the molecules affixed thereto will exhibit an increased circulation time as well as decreased liver uptake. More specifically, the circulation time of the bound molecules is dictated by the maintenance of polymeric structural integrity in vivo. Depolymerization releases bound molecule-DBM monomer, dimer, trimer or like moieties that are themselves rapidly cleared from the recipient's circulation, preferably via the renal pathway.

Depolymerization may be controlled in any convenient manner therefor, including, for example, the following methods:

Use of linkages between dextran units containing chemical groups that are stable in serum for a period of time sufficient to provide an appropriate circulation time to the small molecules bound thereto (e.g., 1 to 3 hours for active agent in both the pretargeting and targeted, direct labeled protocols); or Use of linkages between dextran units that are enzymatically cleaved upon administration of enzyme after the passage of an appropriate amount of bound molecule circulation time.

In the first approach, groups such as esters, acetals, disulfides, thioacetals or the like are employed. For example, an ester linkage, having a serum stability of 1–3 hours such as phenyl or activated phenyl or phthalyl (e.g., chloro-substituted, fluoro-substituted, multi-halogen-substituted, nitro-substituted or the like), may be employed to attach dextran DBM units. Such a linkage is stable in serum for a time sufficient to facilitate localization of the molecules bound to the DBM to the target site.

The second approach includes the use of dextran units susceptible to cleavage by an administrable enzyme that is not found in large amounts in human serum. Exemplary enzymes useful in the practice of this aspect of the present invention include dextranase, alpha-amylase, pullulanase (a bacterial alpha-1,6-polysaccharidase) and the like. The enzymes are administered by any convenient route in any convenient dosage form therefor. Such enzymes are optionally conjugated or formed as fusion proteins with long circulating proteins, including albumin, immunoglobulins or portions thereof, and the like. In this manner, the administered enzymes remain in circulation for a time sufficient to effect depolymerization of the polymer DBM.

In a modified version of this technique, a dextran DBM is employed, which has both targeting moiety and active agent bound thereto in a manner permitting targeting moiety and active agent to be released as a single molecule as depolymerization progresses. For example, dextran units are linkable to both targeting moiety and a radionuclide chelate via a stable linkage. Target binding of these conjugates of the present invention maintains both radionuclide and targeting moiety at the target with both components being released upon DBM depolymerization. For pretargeting approaches, ligand or anti-ligand may be bound to the DBM in a manner to be released separately from or as integrally with an active agent-containing molecule.

Conjugates including internalizing targeting moieties bound to short term serum stable polymers bearing multiple active agents are also contemplated by the present invention. In this manner, multiple active agents can be simultaneously targeted, thereby overcoming active agent delivery problems such as low receptor number or low active agent specific activity. For some methods of the present invention employing internalizing targeting moieties, the linkages (e.g., disulfides, esters, ethers, thioethers, hydrazides and the like) between the dextran units are selected to be cleavable in an intracellular environment (e.g., the acidic environment of a lysosome and the like), or upon target localization of subsequently administered cleaving enzymes are also directed by an internalizing targeting moiety.

Intracellularly cleavable linkers are used when the active agent requires release from the internalized conjugate to exert its diagnostic or therapeutic benefit. Exemplary active agents of this type are drugs and the like. For active agents that do not require intracellular cleavage to exert its diagnostic or therapeutic benefit, the linkage between the DBM and the active agent may be stable to intracellular conditions. Exemplary active agents of this type are radionuclides and the like.

Radiolabeled ligand (e.g., biotin) is an exemplary small molecule capable of directed biodistribution in accordance with the present invention. Other molecules which may show directed biodistribution (i.e., small molecules or larger targeting moieties) consist of or contain drugs, ligands such as biotin, anti-ligands such as avidin and streptavidin, targeting moieties, such as antibodies and peptides specific for target cell receptors (e.g., somatostatin, derivatives thereof such as octreotide and MK-678 (Merck), melanocyte stimulating hormone and the like), epidermal growth factor, chemotactic peptides, c-kit ligand or stem cell growth factor and the like.

Small molecules useful in the practice of the present invention exhibit one or more of the following characteristics: a molecular weight below about 2 kD, lipophilicity, hepatobiliary excretion, ability to bind (directly or indirectly) to DBMs of the present invention and the like. Useful targeting moieties selectively localize to the target cells of interest and are capable of binding (directly or indirectly) to DBMs to form conjugates of the present invention. In addition, useful small molecules and larger targeting moieties preferably exhibit or are derivitizable to exhibit one or more of the following functional groups: aldehyde, maleimide, amine, thiol, alcohol, carboxyl and the like.

A problem encountered in effectively delivering active agent to target cells is created by the recipient's catabolism or metabolism. Catabolic byproducts of administered conjugates (e.g., stable chelate-lysine adducts of antibody-chelate-radionuclide conjugates, such as Tc-99m or Re-186 mercaptoacetylglycylglycyl-gamma-aminobutyryl lysine, Tc-99m or Re-186 4,5-dimercaptoacetamido-pentanoyl lysine and the like) exhibit undesirable biodistribution profiles in that such adducts are subject to hepatobiliary excretion. DBMs of the present invention also preferably direct the excretion of such metabolites to the renal pathway.

Polyglutamate is another example of a DBM useful in the practice of the present invention. Polyglutamate DBMs are structurally capable of delivering multiple active agents per targeting moiety and directing excretion of such active agents to the renal pathway. Exemplary polyglutamate conjugates include chelate-polyglutamate-antibody (Ab) molecules of the following structure:

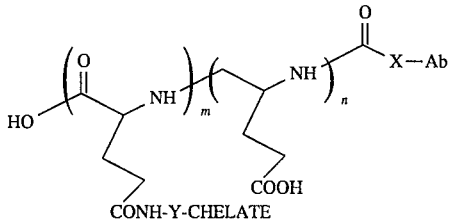

CONH-Y-CHELATE where X is a stable or conditionally unstable (e.g., acid labile, enzyme cleavable, base labile or the like) linkage. For example, X can be —NH— (amide, stable), —NHOCH$_2$CONH— (alkoximine, acid labile) or —O(CH$_2$)$_n$CONH—; n is 1–2 (ester, enzyme cleavable, base labile). Y is a spacer incorporated for synthetic convenience, which can constitute for example, an alkyl or amino acid amide moiety. This moiety contains m carboxylates attached to chelate amino groups (preferably through amino terminus attachment to the antibody-linker to reduce crosslinking) and n free carboxylates. The values of n and m are manipulable by one of ordinary skill in the art to deliver a diagnostic or therapeutic dose of radioactivity to target cells, while maintaining the desired biodistribution profile.

As can be ascertained from an examination of the chelate-DBM-antibody conjugate structure, the number of radionuclides bound to the conjugate ranges between about 0.01x and about 0.1x (where x is the number of units in the polyglutamate polymer, generally ranging between from about 7 and about 50). By delivering more radiometal atoms per antibody targeting molecule, the specific activity of the administered conjugate is enhanced. This feature is shared by the other polymeric DBMs of the present invention.

In addition, the antibody-DBM linkage may be rendered stable (e.g., simple amide linkage), acid labile (e.g., alkoximine linkage) or enzyme cleavable, base labile (e.g., ester linkage). The advantage of using conditionally cleavable linkers is an improvement in target/non-target localization of the active agent. More specifically, use of linkers that are cleaved by enzymes, which are present in non-target tissues but reduced in amount or absent in target tissue, can increase target cell retention of internalized active agent (e.g., targeted by an internalizing targeting moiety) relative to non-target cell retention, because the polymeric DBMs are unlikely to be excreted once internalized into the target cells. For example, ester linkages are susceptible to esterases in the liver and kidney as well as to hydrolysis. Also, alkoximine linkers are susceptible to hydrolysis in the liver and in lysosomes within tumor cells. Such linkers are useful, for example, in delivering therapeutic radionuclides to target cells, because such active agents do not require internalization for efficacy, provided that the linker is stable at the target cell surface or protected from target cell degradation.

Both non-target associated conjugate and active agent-containing metabolites thereof are directed to renal excretion by the polyglutamate DBM. Synthesis of conjugates containing the exemplary stable and conditionally unstable polyglutamyl-antibody linkages are set forth in Example IX hereof.

Other examples of polyglutamate DBM conjugates include DBM-ligand molecules, where, for example, biotin-N-hydroxysuccinimide (NHS) active ester is conjugated to polyglutamyl polymer to form the compound depicted below.

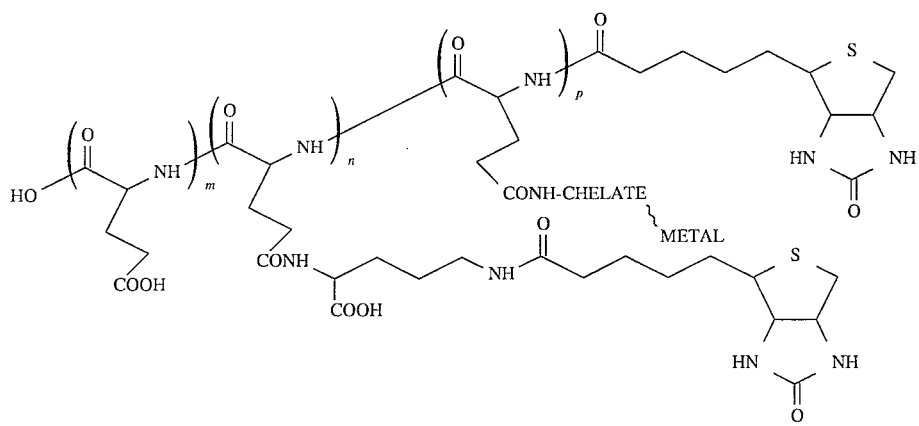

An exemplary synthesis of this molecule is set forth in Example X. Other active esters, such as tetrafluorophenyl or the like may also be employed. This moiety contains p monomers attached to chelate functional groups, n+1 monomers attached to ligand functional groups and m underivitized monomers. The values of n, m and p are manipulable by one of ordinary skill in the art to achieve a therapeutic or diagnostic objective, while maintaining the desired biodistribution profile.

Peptide-polyglutamyl conjugates are prepared, for example, by reacting the activated carboxy terminus of the peptide (e.g., an active ester form of the carboxylic acid group, such as a tetrafluorophenyl ester, a N-hydroxysuccinimide ester or the like) to polyglutamate to form a compound of the structure shown below.

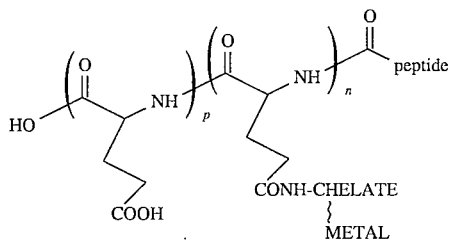

This moiety contains n monomers attached to chelate functional groups (e.g., amines) and p underivitized monomers. The values of n and p are manipulable by one of ordinary skill in the art to achieve a therapeutic or diagnostic objective, while maintaining the desired biodistribution profile.

Chelate conjugation to the exposed acid moieties of the polyglutamate can be conducted for the DBM-biotin and DBM-peptide molecules in substantially the same manner as for the antibody-DBM discussed in Example IX. In addition, multiple chemotherapeutic drugs or other active agents containing, for example, amino or alcohol groups, can be conjugated to the exposed carboxy groups using conventional chemistry therefor.

Another exemplary DBM of the present invention is succinylated polylysine having the following structure:

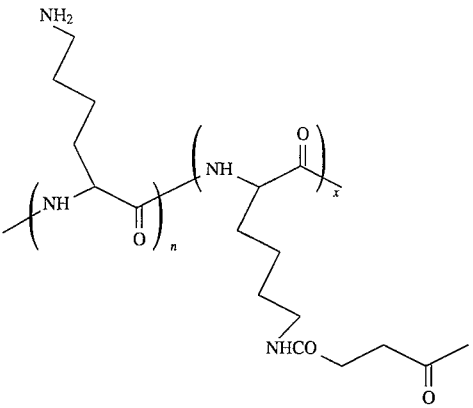

where n ranges from about 25 to about 500, and x ranges from 0 to about 25. Polylysine DBMs are capable of delivering multiple active agents to target cells. Moreover, the succinylation directs the biodistribution of the DBM and, therefore, the DBM-containing conjugates or DBM-containing conjugate metabolites to renal excretion. Exemplary succinylated polylysine conjugates of the present invention include chelate-succinylated polylysine-antibody molecules of the following structure:

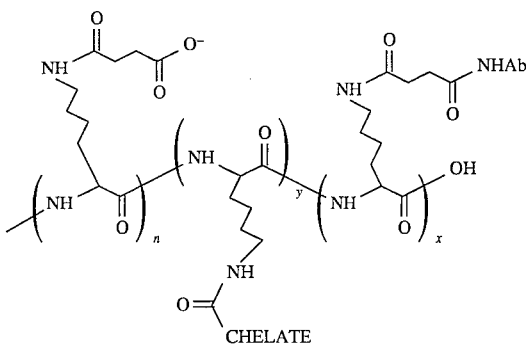

where n ranges from about 16 to about 475; x ranges from about 0 to about 1; and y ranges from about 1 to about 10. These conjugates are prepared, for example, by reacting epsilon amino lysine moieties of the polymer with chelate active esters, such as N-hydroxysuccinimide esters, tetrafluorophenyl esters or the like followed by reaction with succinic anhydride or the like. A carboxylate group (e.g., the carboxy terminus) of the succinylated polylysine is then reacted with an antibody amino group in EDCI. Alternatively, succinylated-polylysine conjugates of the present invention are preparable in accordance with Example XI hereof.

Other examples of succinylated polylysine DBMs of the present invention include DBM-ligand molecules, where, for example, biotin-N-hydroxysuccinimide ester is conjugated to the epsilon amino groups of polylysine to form a compound of the following structure:

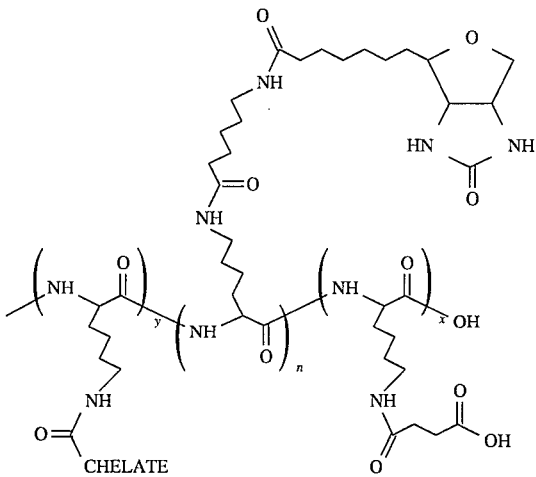

where n ranges from about 1 to about 5; y ranges from about 5 to about 20; and x ranges from about 16 to about 475. Other active esters employable for this purpose are tetrafluorophenyl esters and the like.

Peptide-succinylated polylysine conjugates are prepared, for example, by conjugating the carboxy terminus of the peptide with the polymer epsilon amino groups, resulting in a compound of the structure shown below.

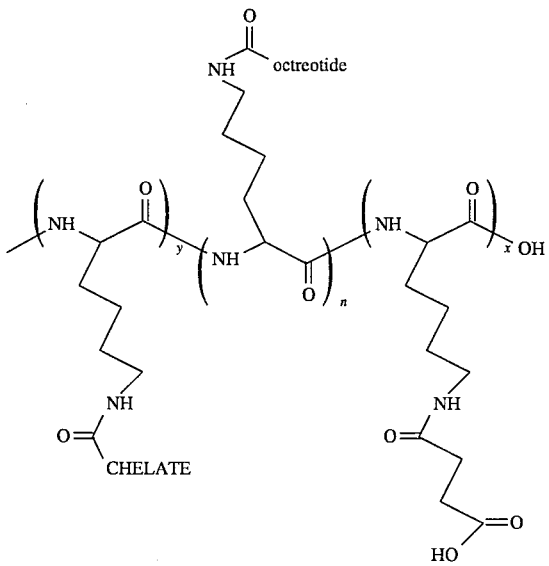

where n ranges from about 1 to about 5; y ranges from about 5 to about 20; and x ranges from about 16 to about 475. To prepare chelate-succinylated polylysine-biotin and chelate-succinylated polylysine-protein conjugates, polylysine is acylated with a serial offering of biotin active ester derivative (or protein) followed by chelate active ester. Succinic anhydride activation is then conducted in accordance with known techniques therefor. Exemplary active esters for this purpose are N-hydroxysuccinimide or the like. The absolute and relative offering ratios of the biotin/peptide and chelate will impact the structure or structure distribution of the final product. Derivitization of the DBM adversely impacts the biodistribution directing properties thereof. Consequently, more heavily derivitized DBM is less likely to properly direct the biodistribution of bound molecules in accordance with the present invention. Preferably, the molecular weight of the DBM is >>the molecular weight of the molecules bound thereto.

Another aspect of the present invention involves lower molecular weight DBMs (i.e., ranging from about 500 to about 2000 Dal.) of high polarity. Preferably, DBMs of this aspect of the present invention are highly charged, i.e., greater than about 2 ionic charges/1000 dalton moleculra weight. An exemplary DBM of this aspect of the present invention is diethylene triamine pentaacetic acid (DTPA described by Hnatowich, *IJARI*, 33: 327–333, 1982); DTPA derivatives (e.g., carbon-backbone substituted DTPA derivatives, such as SCN-Bz-DTPA); ethylenediamine tetraacetic acid (EDTA); aminotriacetic acid (NTA); ethylene glycoldiamino tetraacetic acid (EGTA); other polyimino acetic acids; 1,4,7,10-tetraazacyclododecane-N,N',N'',N'''-tetra acetic acid (DOTA) derivative or other polycarboxylic acid molecule; and the like. DTPA and DOTA and derivatives thereof are preferred DBMs in the practice of this aspect of the present invention.

Imaging studies of tumor and infection by pretargeting with avidin generally involve biotin labeled with In-111, with In-bis-biotin-DTPA being the most commonly employed moiety. In-bis-biotin-DTPA is water soluble and contains regions of positive and negative charge imparted by tertiary amines and carboxylates, respectively. DTPA has been conjugated to octreotide for the purpose of labeling octreotide with In-111 (*J. Nucl. Med.*, 33: 652–658, 1992).

Very little study has been reported with respect to technetium labeling of biotin. Virzi et al., "The preparation and evaluation of 12 biotin derivatives labeled with Tc-99m," *J. Nucl. Med.*, 1192, 33:5, 920 (abstract) discuss aminothiol and polyaminocarboxylate chelating agents, resulting in conjugates of poor in vivo stability.

The present invention provides stable biotin-DTPA conjugates, such as the following:

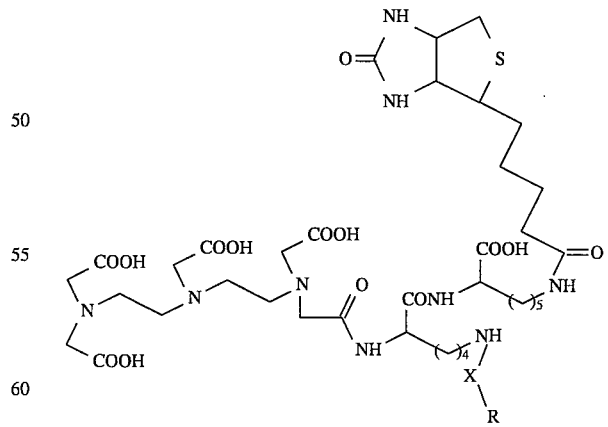

where R is a chelate and X is a spacer included in the structure for synthetic convenience. More specifically, X is preferably a carbonyl spacer, such as —CO—, —CO—(CH$_2$)—, —COCH$_2$NHCO— or the like. For rhenium radionuclides, R is preferably an N$_2$S$_2$ or an N$_3$S amidothiolate chelate. Also preferred in the practice of the present invention are iodobenzamide chelate-DBMs, where X is preferably a carbonyl spacer, —CO—, and R is preferably p-iodophenyl (PIP).

The above-identified conjugate employs a lysine amino acid group to link the ligand to the DBM and to link the chelate to the DBM. Other groups useful for this purpose include amino acids, such as aspartic acid, glutamic acid, serine, threonine, cysteine and the like; synthetic compounds containing appropriate functional groups, such as carboxylic acid, amine, alcohol or thiol; or the like. The structure shown above depicts the ligand attached to the amino terminus of lysine, with active agent attachment to the epsilon amino group thereof. Other options include the following:

- ligand to carboxy terminus/active agent to epsilon amino group;
- ligand to epsilon amino group/active agent to carboxy terminus;
- ligand to carboxy terminus/active agent to amino terminus; and
- ligand to amino terminus/active agent to carboxy terminus.

The stable DTPA conjugates of the present invention direct the biodistribution of molecules associated therewith (particularly small molecules) to renal excretion. In this manner, small molecule (especially active agent) hepatobiliary excretion is decreased.

These embodiments of the DBMs of the present invention are prepared, for example, in accordance with the reaction mechanism set forth and described in Example VII herein. Briefly, a protected lysine-biotin conjugate (or other similar biotin derivative, such as glutamic acid biocytinamide or the like) is prepared; DTPA anhydride is opened with the lysine-biotin (or other derivative); the lysine (or other reactive moiety) is deprotected; the amine (or other functional group) is acylated with an active ester chelate, such as tetrafluorophenyl esters, N-hydroxysuccinimide esters and the like. A useful protecting group for this purpose is

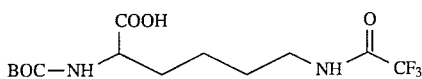

An alternative reaction scheme employing a different protection/deprotection strategy may be used in the practice of these embodiments of the present invention. In this alternative scheme, the following protecting group is employed.

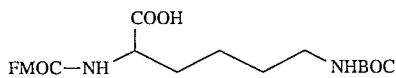

As a result, the alternative reaction scheme proceeds as described above and in Example VII herein, with the most notable exception being that the deprotection of the epsilon lysine amino group involves TFA cleavage of BOC.

It is useful to note that DTPA is itself a chelate and has been used as such for radionuclides such as In-111 and Y-90. Consequently, precomplexation of the DTPA chelate may be necessary to form conjugates of the present invention involving a radionuclide chelate bound to a DTPA DBM. Preferred chelates used in the practice of the present invention (e.g., $N_xS_y$ compounds and the like) may not require such precomplexation. The radionuclide-chelate complexes formed by the preferred chelates are generally thermodynamically more stable than the DTPA complexes thereof. Consequently, at the conditions employed for radiolabeling with, (e.g., Tc-99m, Re-186, Re-188 and the like), the radionuclide typically transchelates from the DTPA core to the preferred chelate core.

An example of another embodiment of the conjugates of the present invention includes has the formula set forth below:

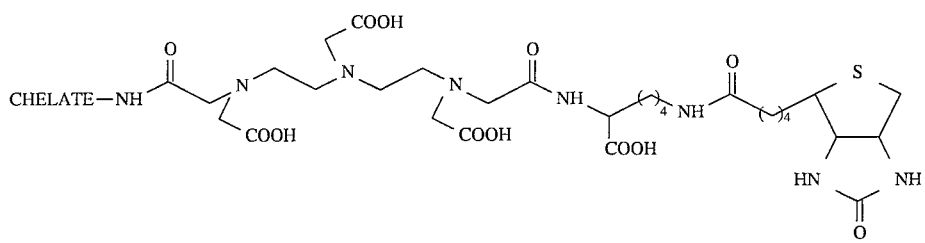

In this embodiment of the present invention one small molecule is attached to a carboxylate moiety of DTPA, while another small molecule is bound to a second carboxylate moiety thereof. These embodiments of the DBMs of the present invention are prepared, for example, in accordance with the reaction mechanism set forth and described in Example VII(C) herein.

These stable DTPA conjugate embodiments of the present invention direct the biodistribution of molecules associated therewith to renal excretion. In this manner, small molecule (especially active agent) hepatobiliary excretion is decreased.

Peptides may also be conjugated to DTPA derivatives in accordance with the present invention. The strategy for preparing, for example, a radiolabeled chelate- peptide-DTPA conjugate involves the preparation of a chelate-peptide conjugate which contains a free amino group for reacting with DTPA anhydride to form an amide linkage between a DTPA carboxylate group and a chelate or peptide amine group. For a peptide amenable to reaction with a chelate amine group, the following procedure may be employed to form a chelate-peptide conjugate. Briefly, a $N_3S$ trifluorophenyl ester is reacted with ethylene diamine in $CH_3CN$ to form an amide linkage and generate a chelate with a free amine. This chelate is reacted with BOP and DIEA (diethylamine) to form a chelate-peptide conjugate through reaction with an unprotected peptide carboxylate group (e.g., the acid moiety of an aspartic acid or of a glutamic acid amino acid). An unprotected amine group of the chelate-peptide conjugate (e.g., a lysine epsilon amino group) is reacted with a DTPA anhydride to form the product chelate-peptide-DBM conjugate. Preferably, the amine group employed in the ultimate conjugation is protected during the previous steps to avoid the generation of undesirable byproducts. TFA is exemplary of protecting groups that are employable for this purpose.

Alternatively, replacement of a glycine by a lysine in a N₃S chelate, i.e., mercaptoacetylglycylglycyl-gamma-amino butyric acid (MAGG-GABA) chelate modified as described above with ethylene diamine in CH₃CN, provides an amino group for reaction with an unprotected peptide carboxylate group (e.g., the acid moiety of an aspartic acid or a glutamic acid amino acid) to form a chelate-peptide conjugate using analogous chemistry to that employed in the reaction scheme discussed above. The derivitized chelate is prepared in accordance with the following reaction scheme.

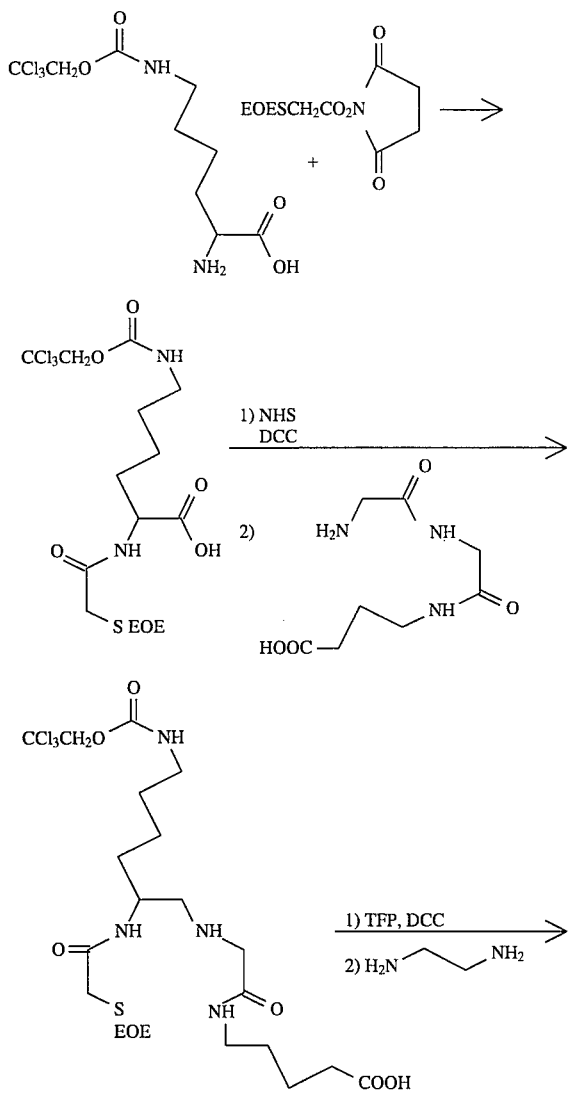

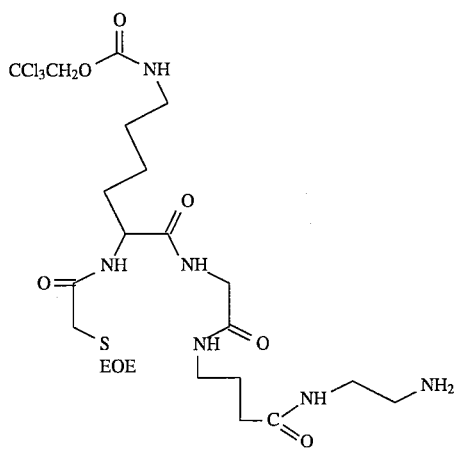

The derivitized chelate also has an amino group available for subsequent reaction with DTPA anhydride to form the product DBM-chelate-peptide using analogous chemistry to the reaction scheme discussed above. Preferably, the amino group involved in the DBM conjugation is protected during the chelate-peptide conjugation. Any amino groups on the peptide are preferably protected until formation of a DBM-chelate-peptide molecule.

Another alternative involves derivitization of the peptide to provide an amino group for reaction with DTPA anhydride. A peptide lysine, for example, can be reacted with, for example, the following compound

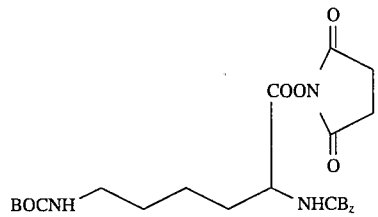

to provide one protected amino group which can be deprotected with TFA and a second protected amino group which can be deprotected with hydrogen. The derivitized peptide is reacted with TFA, and the unprotected amine is then exposed to DTPA anhydride to form a peptide-DBM conjugate with a protected amine group. The conjugate is exposed to hydrogen to form a versatile intermediate that is reactive with a variety of chelate active esters to form a DBM-chelate-peptide conjugate. During this synthesis, any other amino groups on the peptide are preferably protected. TFA is an exemplary protecting group useful for this purpose.

Antibodies or antibody fragments may also be conjugated to DTPA DBMS of the present invention. An exemplary procedure for this synthesis is discussed in Example VIII hereof.

Another embodiment of the present invention features cyclic DTPA DBMs of the following formula:

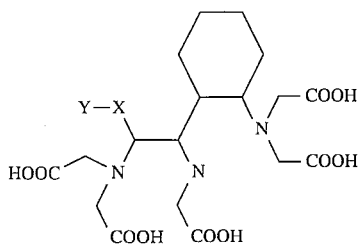

wherein X is a linking group and Y is a small molecule. Small molecules that are preferably used in this embodiment of the present invention are radiolabeled biotin, drugs, peptides, chelates and the like. Preferred linking groups useful in the cyclic DTPA DBM embodiments of the present invention are amides, esters, ethers, thioethers and the like. Conjugates of this aspect of the present invention are preparable using the techniques described herein for small molecule conjugation to DTPA. Cyclic DTPA synthesis is known in the art.

In addition, the present invention contemplates complexation of the DTPA core with a nonradioactive metal, such as iron, indium, gallium, aluminum or the like. An exemplary conjugate of the present invention incorporating such a DTPA core-complexed DBM is shown below.

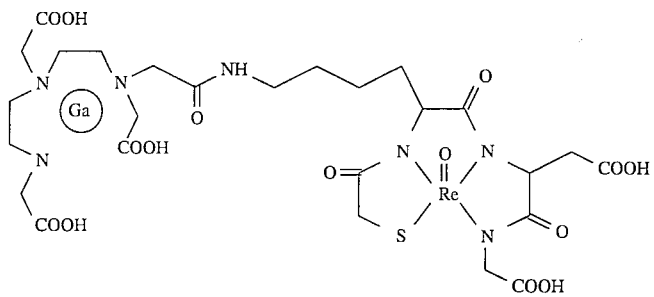

Other small molecules (.e.g., peptides, ligands, anti-ligands, chelates or the like) may also be incorporated into these conjugates of the present invention.

Preparation of DTPA core-complexed DBM conjugates of the present invention which also include a radionuclide-chelate complex may be conducted in several ways. If the radionuclide preferably binds to the chelate rather than the DTPA core, the conjugate may be radiolabeled with the radionuclide with subsequent complexation with the nonradioactive metal. The nonradioactive metal complexation can be conducted first, provided that the nonradioactive metal preferentially binds to DTPA and the resultant metal-DTPA complex is stable with respect to radionuclide chelation conditions. Some rhenium labeling protocols, for example, require a powerful reducing agent (stannous chloride) and heat.

Alternatively, a procedure that does not require selective binding of a metal in the presence of two uncomplexed chelators can be employed. An exemplary procedure of this type involves chelating DTPA anhydride with a trivalent metal prior to conjugation thereof with the chelate. Subsequently, the metal-DTPA-chelate is radiolabeled with rhenium.

Another conjugate that is the subject of the present invention is an improved 1,4,7,10-tetraazacyclododecane-N,N',N'',N'''-tetra acetic acid (DOTA) derivative or other polycarboxylic acid molecules. DOTA has been employed to deliver Y-90 to target cells and described by Renn and Meares for Y-90 in *Bioconjugate Chem.*, 3:563–569, 1992. A problem with such delivery is an inability to follow the in vivo localization of the conjugates over time with gamma camera imaging, because Y-90 is not a gamma-emitter. In clinical trials, for example, it is very important to identify normal organ distribution of a conjugate incorporating a radionuclide to determine the maximum safe dose that can be administered to recipients. Procedures for obtaining biodistributions are also complicated by the lack of gamma emission, necessitating indirect measurement of bremstrahlung from the beta-decay of Y-90. These problems are overcome in using a compound of the following formula:

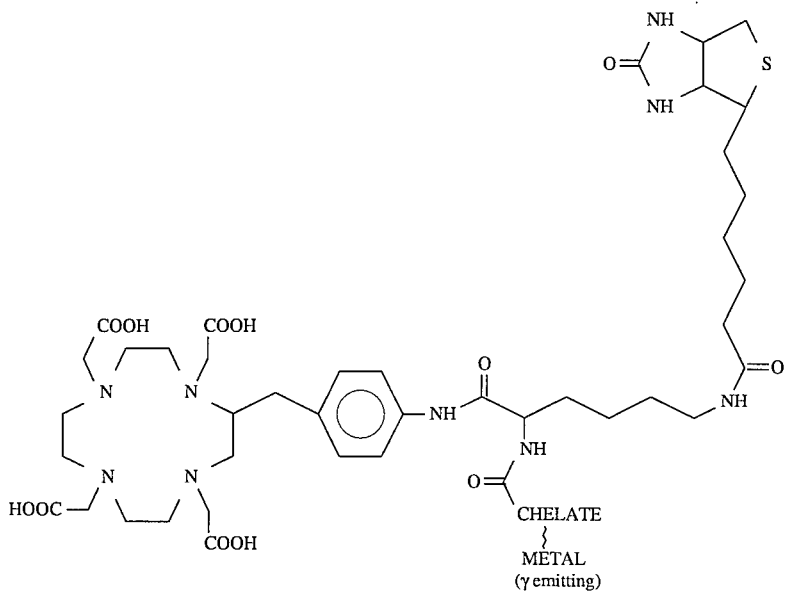

These conjugates of the present invention are characterized by the attachment of a gamma-emitting radionuclide (e.g., In-111, Tc-99m, Re-186, Re-188 or the like) to the biotin side chain and the retention of Y-90 in the DOTA core. The chelate component of the conjugates of this embodiment of the present invention is selected based upon the radionuclide to be complexed therein. Exemplary chelates for use in this embodiment are $N_xS_y$ chelates for rhenium and technetium, DTPA or DOTA for In-111 and the like. The conjugates of this aspect of the present invention can be prepared in accordance with one of the two schemes shown below.

Scheme 1:

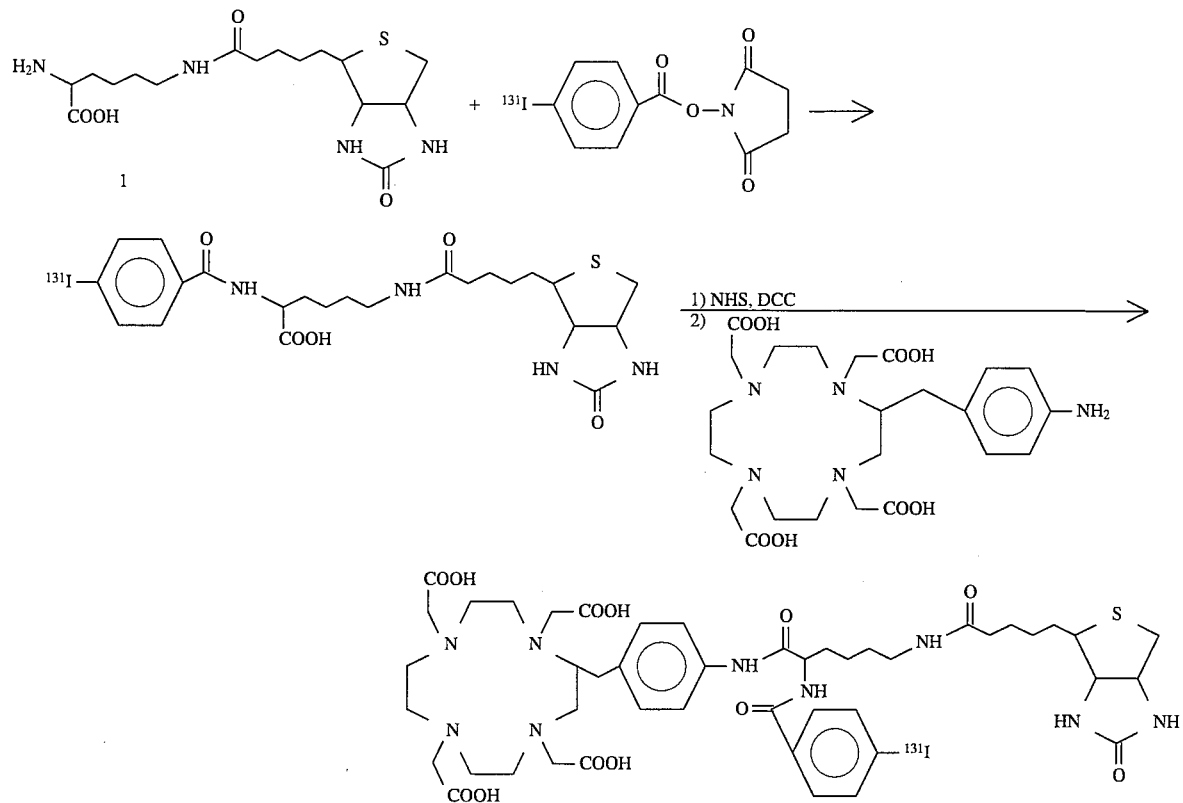

Scheme 2:
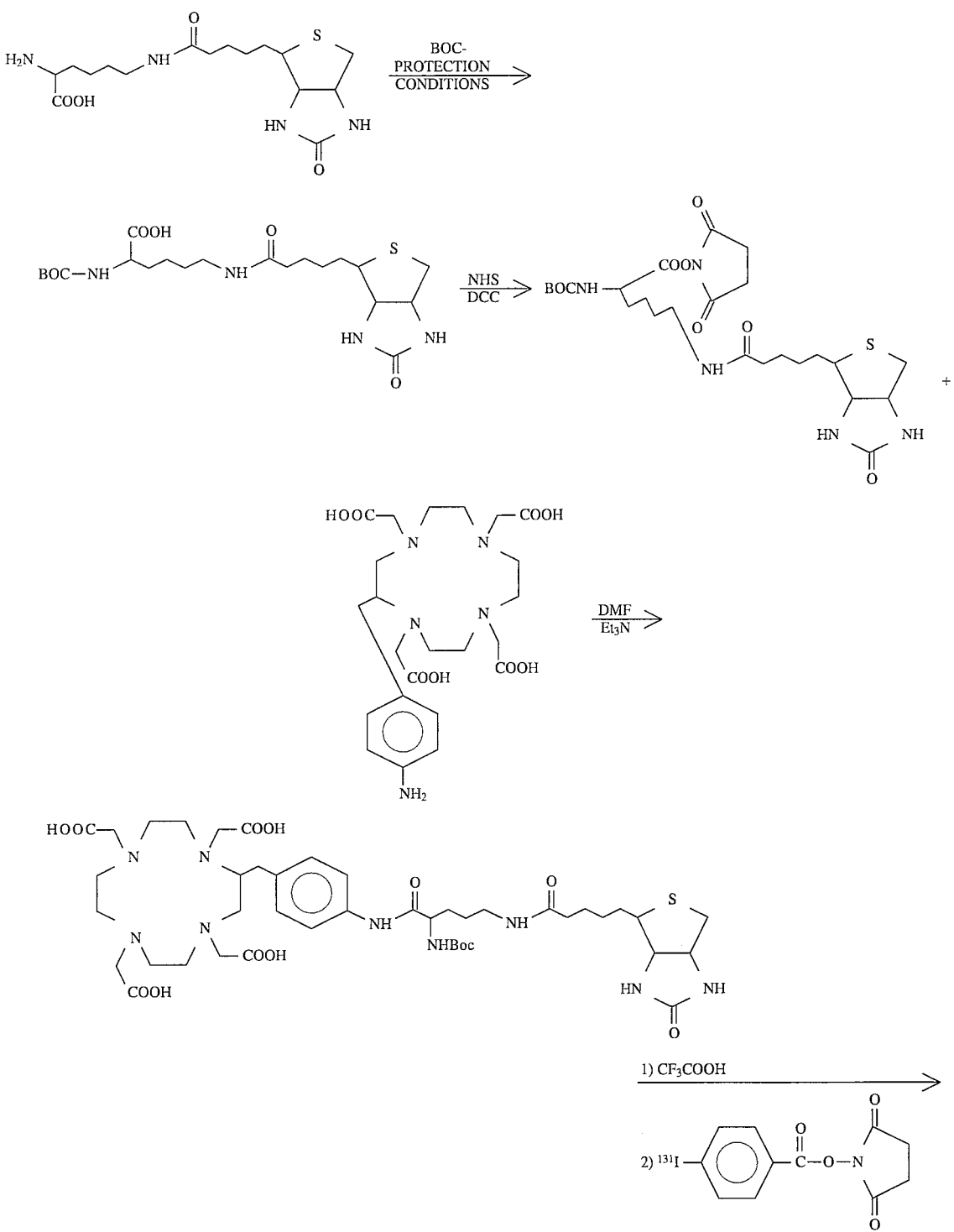

-continued
Scheme 2:

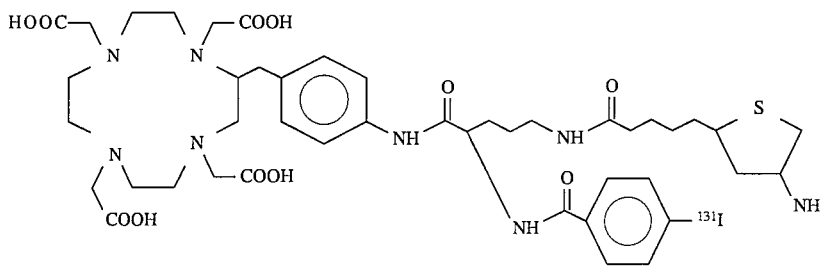

These conjugates of the present invention can be followed by gamma camera imaging and direct biodistribution data thereof can be obtained. In addition, the renal excretion properties of DOTA direct the distribution of the radionuclides bound to the biotin conjugate component, thereby serving as a DBM in the manner of the DTPA derivatives described above.

EXAMPLE I

Synthesis of Chelate-Ligand Conjugates and DBM-Chelate-Radionuclide Conjugate Preparation: Tentacle Method A. Preparation of Iodine Chelate-Ligand.

Preparation of radioiodinated biotin according to the following method provides certain advantages. First, the radioiodobiotin derivative is a low molecular weight compound that is amenable to complete chemical characterization. Second, the disclosed methods for preparation involve a single step and eliminate the need for a purification step.

Briefly, iodobenzamide derivatives corresponding to biocytin (R=COOH) and biotinamidopentylamine (R=H) were prepared according to the following scheme. In this scheme, "X" may be any radiohalogen, including $^{125}I$, $^{131}I$, $^{123}I$, $^{211}At$ and the like.

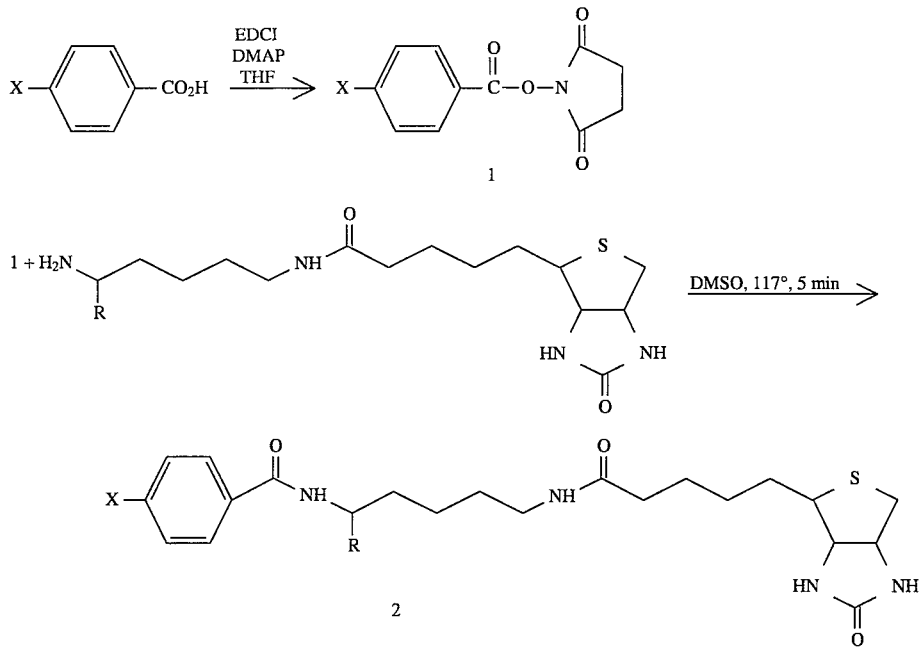

Radioiodinated biotin derivatives prepared by exposure of poly-L-lysine to excess NHS-LC-biotin and then to Bolton-Hunter N-hydroxysuccinimide esters in DMSO has been reported. After purification, this product was radiolabeled by the iodogen method (see, for instance, Del Rosario et al., *J. Nucl. Med.* 32:5, 1991, 993 (abstr.)). Because of the high molecular weight of the resultant radioiodinated biotin derivative, only limited characterization of product (i.e., radio-HPLC and binding to immobilized streptavidin) was possible.

Preparation of 1 was generally according to Wilbur et al., *J. Nucl. Med.* 30:216–26, 1989, using a tributyltin intermediate. Water soluble carbodiimide was used in the above-depicted reaction, since the NHS ester 1 formed intractable mixtures with DCU. The NHS ester was not compatible with chromatography; it was insoluble in organic and aqueous solvents and did not react with biocytin in DMF or in buffered aqueous acetonitrile. The reaction between 1 and biocytin or 5-(biotinamido) pentylamine was sensitive to base. When the reaction of 1 and biocytin or the pentylamine was performed in the presence of triethylamine in hot DMSO, formation of more than one biotinylated product resulted. In contrast, the reaction was extremely clean and complete when a suspension of 1 and biocytin (4 mg/ml) or the pentylamine (4 mg/ml) was heated in DMSO at 117° C. for about 5 to about 10 min. The resultant $^{125}$I-biotin derivatives were obtained in 94% radiochemical yield. Optionally, the radioiodinated products may be purified using C-18 HPLC and a reverse phase hydrophobic column. Hereinafter, the resultant radioiodinated products 2 are referred to as PIP-biocytin (R=COOH) and PIP-pentylamine (R=H).

B. Preparation of Technetium and Rhenium Chelate-Ligand.

A chelating compound that contains an $N_3S$ chelating core was attached via an amide linkage to biotin. Radiometal labeling of an exemplary chelate-biotin conjugate is illustrated below.

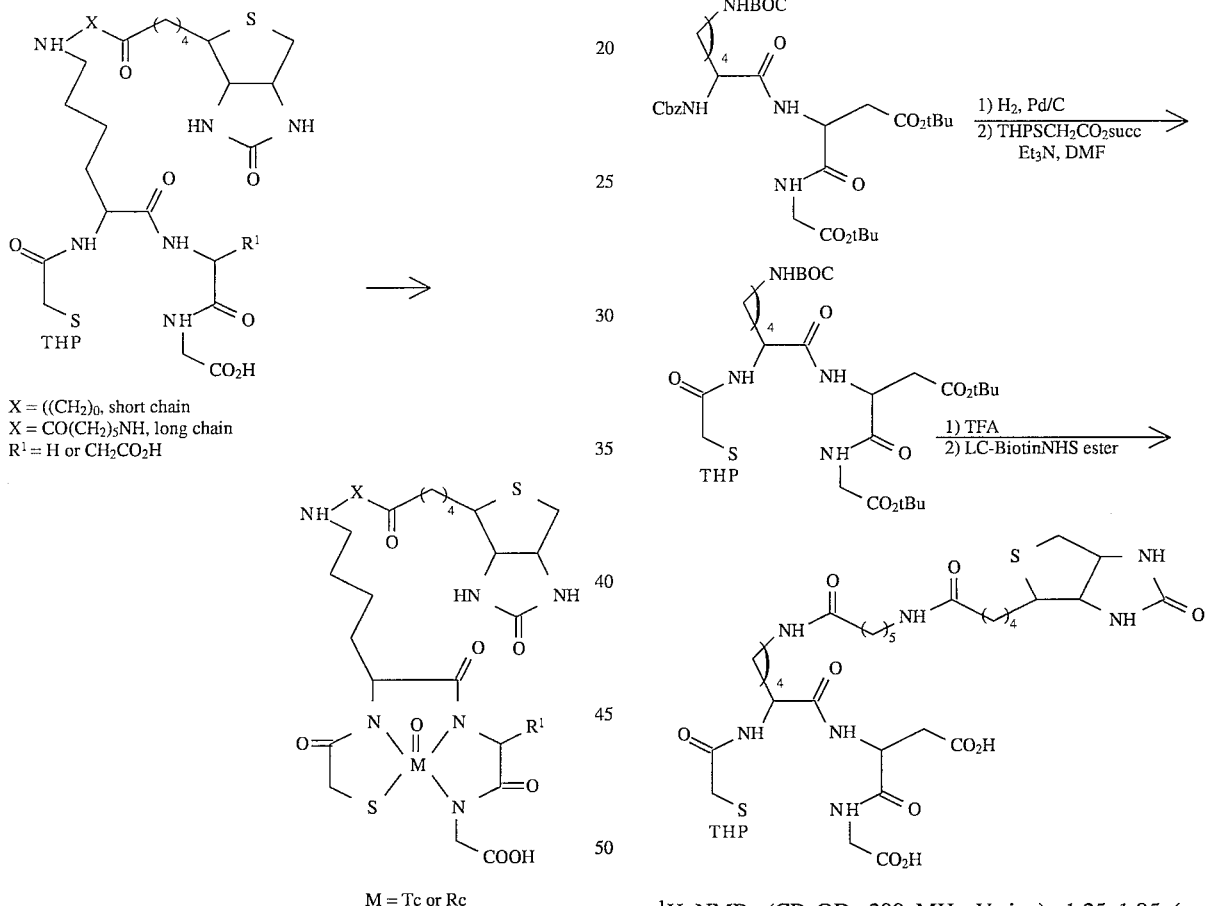

M = Tc or Re

The spacer group "X" permits the biotin portion of the conjugate to be sterically available for avidin binding. When "R$^1$" is a carboxylic acid substituent (for instance, CH$_2$COOH), the conjugate exhibits improved water solubility, and further directs in vivo excretion of the radiolabeled biotin conjugate toward renal rather than hepatobiliary clearance.

Briefly, N-α-Cbz-N-Σ-t-BOC protected lysine was converted to the succinimidyl ester with NHS and DCC, and then condensed with aspartic acid β-t-butyl ester. The resultant dipeptide was activated with NHS and DCC, and then condensed with glycine t-butyl ester. The Cbz group was removed by hydrogenolysis, and the amine was acylated using tetrahydropyranyl mercaptoacetic acid succinimidyl ester, yielding S-(tetrahydropyranyl)-mercaptoacetyl-lysine. Trifluoroacetic acid cleavage of the N-t-BOC group and t-butyl esters, followed by condensation with LC-biotin-NHS ester provided (Σ-caproylamide biotin)-aspartyl glycine. This synthetic method is illustrated below.

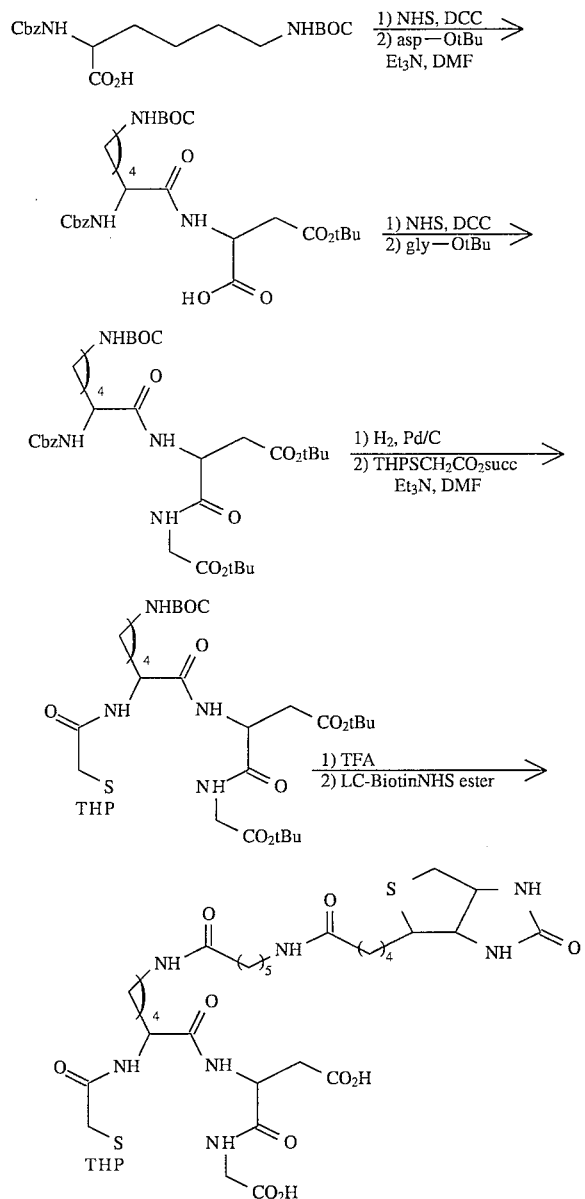

$^1$H NMR: (CD$_3$OD, 200 MHz Varian): 1.25–1.95 (m, 24H), 2.15–2.25 (broad t, 4H), 2.65–3.05 (m, 4H), 3.30–3.45 (dd, 2H), 3.50–3.65 (ddd, 2H), 3.95 (broad s, 2H), 4.00–4.15 (m, 1H), 4.25–4.35 (m, 1H), 4.45–4.55 (m, 1H), 4.7–5.05 (m overlapping with HOD).

Elemental Analysis: C, H, N for $C_{35}H_{57}N_7O_{11}S_2 \cdot H_2O$ calculated: 50.41, 7.13, 11.76 found: 50.13, 7.14, 11.40

The chelate-biotin conjugate was radiolabeled with either $^{99m}$Tc pertechnetate or $^{186}$Re perrhenate. Briefly, $^{99m}$Tc pertechnetate was reduced with stannous chloride in the presence of sodium gluconate to form an intermediate Tc-gluconate complex. The chelate-biotin conjugate was added and heated to 100° C. for 10 min at a pH of about 1.8 to about 3.3. The solution was neutralized to a pH of about 6 to about 8, and yielded an $N_3S$-coordinated $^{99m}$Tc-chelate-biotin conjugate. C-18 HPLC gradient elution using 5–60% acetonitrile in 1% acetic acid demonstrated two anomers at 97% or greater radiochemical yield using 6 (gamma ray) detection.

Alternatively, $^{186}$Re perrhenate was spiked with cold ammonium perrhenate, reduced with stannous chloride, and complexed with citrate. The chelate-biotin conjugate was added and heated to 90° C. for 30 min at a pH of about 2 to 3. The solution was neutralized to a pH of about 6 to about 8, and yielded an $N_3S$-coordinated $^{186}$Re-chelate-biotin conjugate. C-18 HPLC gradient elution using 5–60% acetonitrile in 1% acetic acid resulted in radiochemical yields of 85–90%. Subsequent purification over a C-18 reverse phase hydrophobic column yielded material of 99% purity.

C. DBM-Chelate-Radionuclide Conjugate Preparation Employing the Tentacle Chelate Method. Polylysine (approximately 10,000 Dal. molecular weight, available from Sigma Chemical Co., St. Louis, Mo.) and dextran (lysine fixable, available from Sigma Chemical Co.) were derivitized with SPDP and purified from unreacted SPDP using size exclusion chromatography (using a PD-10 column available from Pharmacia, Piscataway, N.J.). The resultant SPDP-derivitized adducts were reduced with DTT in pH 4.7 0.2M NaOAc buffer to generate free reactive thiols. Reduced Tc, generated from stannous gluconate as described, for example, by Carlsson et al., *Biochem. J.*, 173: 723–737, 1978, was added. A 90% incorporation of Tc was obtained for the polylysine adduct within 15 min, as measured by ITLC. 96% of the radioactivity coeluted with the dextran using size exclusion (PD-10) chromatography. These results are indicative of chelation.

EXAMPLE II

Synthesis of Chelate-Ligand-Dextran-Conjugates

The reaction scheme for this synthesis is shown below.

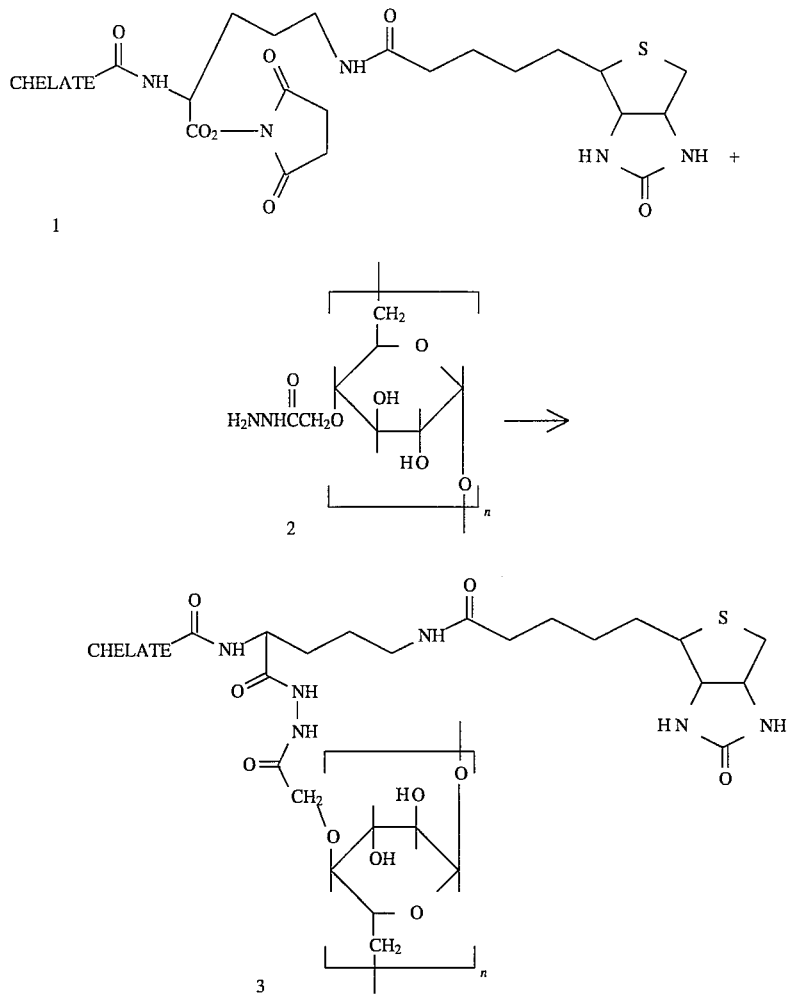

where n ranges from about 50 (10,000 kD polymer) to about 500 (70,000 kD polymer). In this methodology, a chelate-ligand conjugate is prepared in accordance with any convenient procedure therefor (e.g., the procedures described in Examples I and IV hereof). Preferably the chelate-ligand conjugate structure includes a free carboxyl group. The free carboxy group is derivitized under conditions sufficient to generate an active ester (e.g., EDCI, DMAP and THF as described in Example I(A) hereof), with an exemplary active ester chelate-ligand starting material is shown as 1. Dextran hydrazide 2 is conjugated with 1 to give the product dextran-(chelate-ligand)$_n$3.

EXAMPLE III

Radiolabeling Biotin-Dextran, Lysine Fixable and Biodistribution of Radiolabeled Biotin-Dextran A. Preparation Protocol. A solution of 3.0 mg biotin-dextran, lysine fixable (BDLF, available from Sigma Chemical Co., St. Louis, Mo.) in 0.3 ml PBS and 0.15 ml 1M sodium carbonate, pH 9.25, was added to a dried residue (1.87 mCi) of N-succinimidyl p-I-125-iodobenzoate prepared in accordance with Wilbur, et al., *J. Nucl. Med.*, 30: 216–226, 1989.

B. Analysis and Biodistribution. After 45 minutes at room temperature, the solution was passed through a G-25 gel filtration PD-10 column (Pharmacia) and 1 ml fractions were collected. Evaluation of fraction 4, containing 0.66 mCi (35%) of the total radioactivity, by HPLC (BioRad Biogel TSK 50-XL) showed 97.9% of the activity in a peak eluting at 11.47 minutes. By molecular weight standards, the elution time is consistent with a 10,000 molecular weight species. A single broad radiometric brand at 13.4 minutes was observed by HPLC using a Sephacryl S-200 column.

Incubation of an aliquot of fraction 4 with immobilized streptavidin resulted in binding of 76% of the total radioactivity to the immobilized streptavidin. This result is indicative of the presence of intact biotin bound to the radioiodinated dextran.

Biodistribution studies were conducted on radiolabeled biotin-dextran and radiolabeled PIP-biocytin preparable in accordance with the procedure outlined in Example I. The results of those studies are shown in FIGS. 1A (intestine), 1B (bladder) 1C (liver), 1D (kidney) and 1E (blood clearance). These results show that iodine labeled biotin-dextran exhibits a dramatic increase in urinary excretion in comparison to PIP-biocytin. In addition, the biotin-dextran molecule shows much lower hepatobiliary excretion than PIP-biocytin, indicating that the lipophilic biotin molecule is "masked" by the hydrophilic, polar dextran and is therefore subject to renal excretion.

EXAMPLE IV

Rhenium Radiolabeling of BDLF: The Pre-Formed and the Post-Formed Approaches; Technetium Labeling of BDLF A. The Post-Formed Approach. The reaction scheme for this synthesis is shown below.

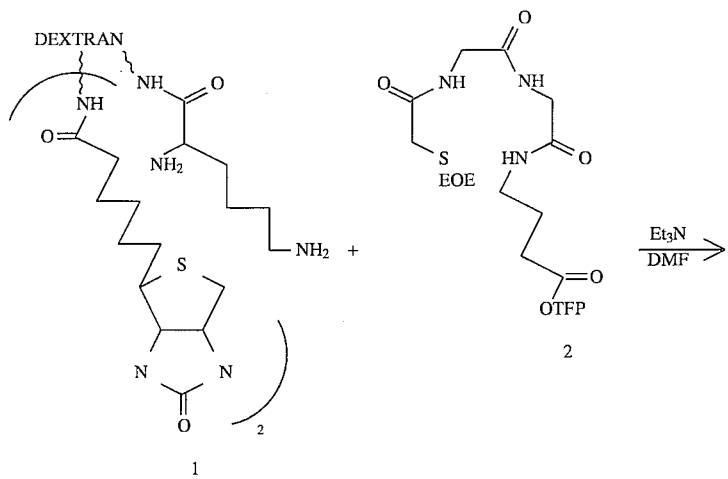

-continued

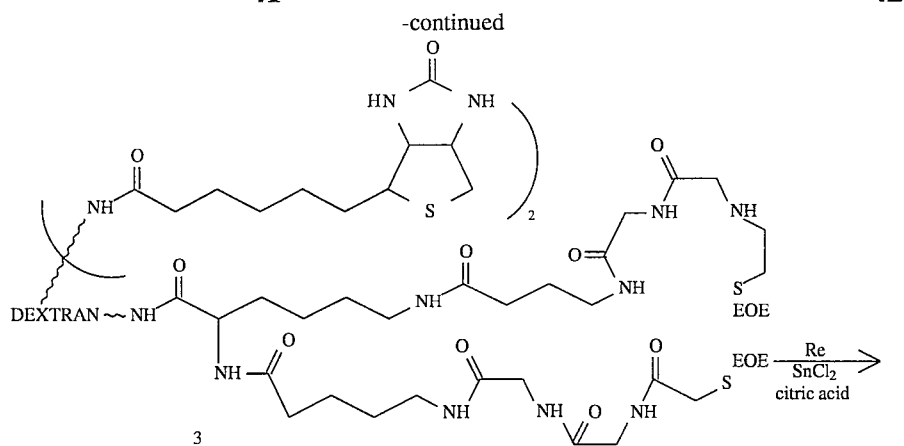

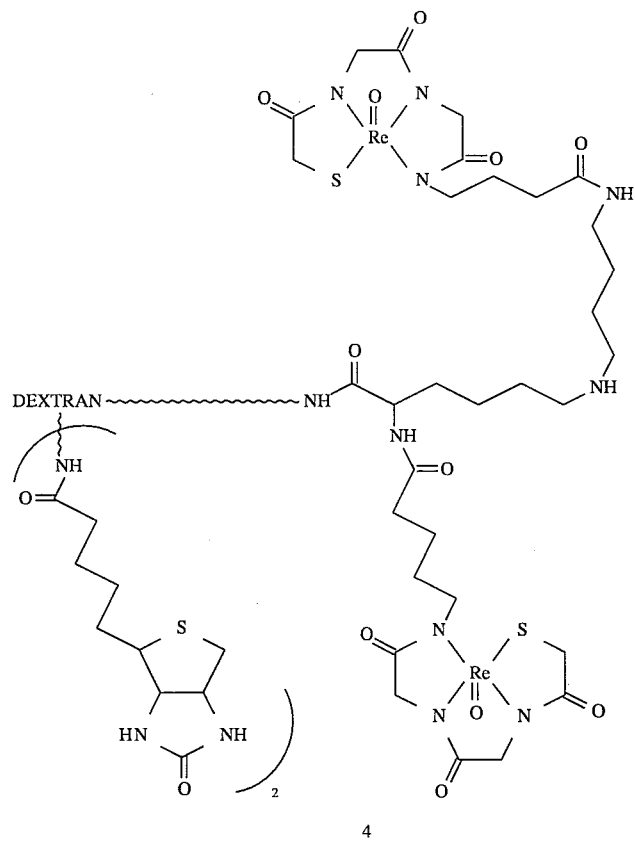

BDLF 1 is condensed with an $N_3S$ chelate tetrafluorophenyl ester 2 under basic conditions, e.g., $Et_3N$ and DMF, $Et_3N$ and DMSO or $NaHCO_3$ and water, to form a chelate-BDLF conjugate 3 through the formation of an amide bond, for example, at the lysine epsilon amino group of 1. Rhenium is complexed within the chelate component of 3 using known techniques therefor, e.g., reduction of perrhenate from aqueous solution conducted under elevated temperature in the presence of tin chloride and citric acid (or as otherwise described in U.S. Pat. No. 4,965,392), to form the product radionuclide chelate-BDLF conjugate 4. Post-formed chelating methodologies are preferred for use with reactants and products that are stable to acidic conditions and heat that are required for the chelation step. Post-formed chelation is more convenient for kit formation, because it involves a single vial kit (i.e., radioactivity is added to a vail containing BDLF-chelated conjugate).

B. The Pre-Formed Approach. The reaction scheme for this synthesis is shown below.

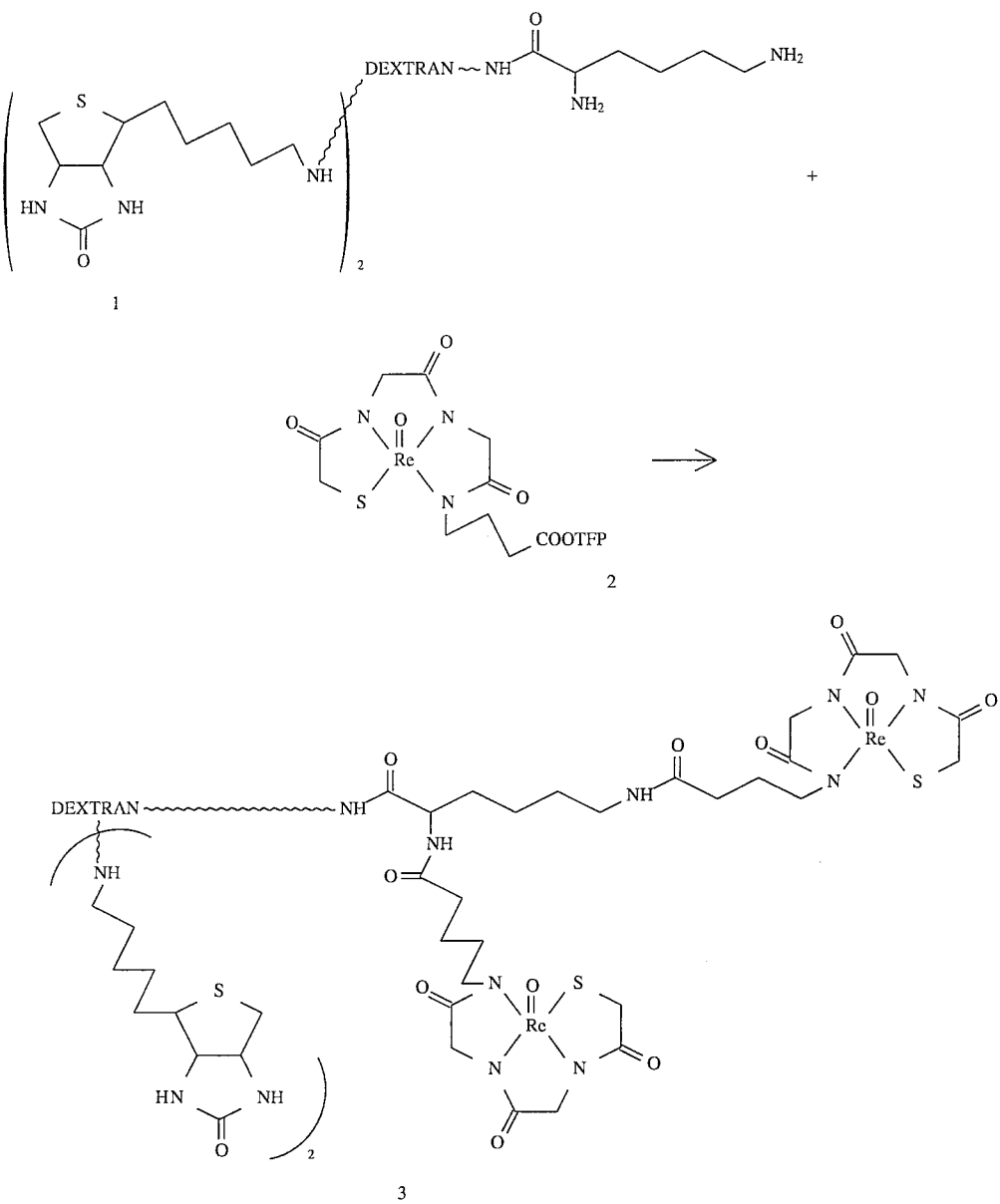

BLDF 1 is reacted with a tetrafluorophenyl ester of a rhenium conjugated N₃S chelate 2 prepared, for example, in accordance with procedures described in U.S. Pat. No. 4,965,392. This reaction preferably is conducted under basic conditions to facilitate the formation of the BDLF-radiolabeled chelate product 3, wherein the chelate is bound to a lysine epsilon amino group of BDLF. Exemplary conjugation conditions are also discussed in U.S. Pat. No. 4,965,392. The pre-formed methodology has the following advantages: only a single step of the procedure for DBM-chelate conjugation involves the DBM and the DBM is not exposed to labeling conditions, which are potentially harmful to the DBM.

C. Technetium Labeling of BDLF. To a solution of 3.2 mg (0.32 µmol) of BDLF (Sigma Chemical Co.) in 1.0 ml PBS and 0.1 ml 0.5M borate buffer, pH 8.5, was added 50 µl (2.5 mg, 8 µmol) of a DMSO solution of N-succinimidyl 3-(2-pyridyldithio)propionate (SPDP). After 1 hour of mixing at room temperature, derivitized BDLF was isolated from unreacted SPDP by G-25 size exclusion chromatography (PD-10, Pharmacia).

Approximately 1 mg of SPDP-BDLF (0.60 ml) was reduced by addition of 0.22 ml (2.25 mg) of dithiothreitol (DTT) in PBS. After mixing at room temperature for 0.5 hours, reduced SPDP-BDLF was isolated by G-25 (PD-10) size exclusion chromatography. A positive DTNB test on the isolated material was indicative of reactive thiols.

Tc-99m labeling was performed by addition of 2.1 mCi Tc-gluconate, which was prepared as discussed in Kasina et al., *J. Nucl. Med.*, 32:1445, 1991, to approximately 0.5 mg (1.0 ml) of reduced SPDP-BDLF. After 30 minutes at room temperature, the labeled adduct was isolated in 92% radiochemical yield by G-25 (PD-10) chromatography.

EXAMPLE V

Radiolabeled Antibody-Dextran Conjugate Synthesis

A. From Carboxymethyl Dextran. The reaction scheme for this synthesis is shown below.

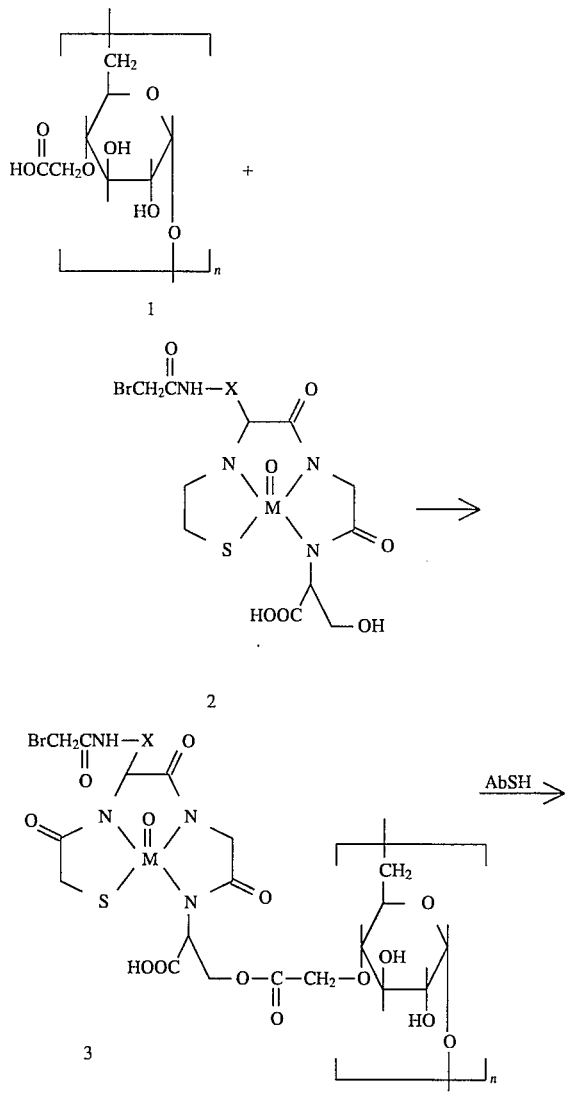

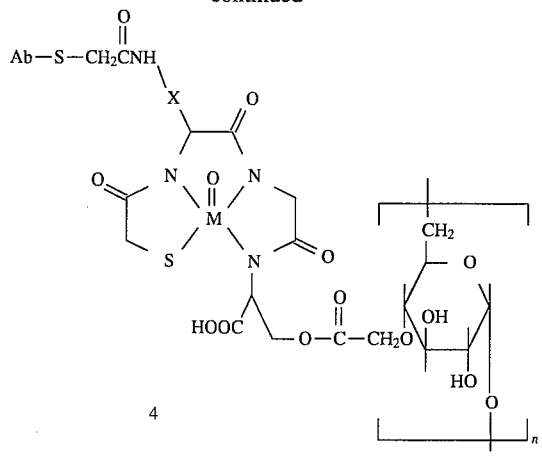

where X is selected from alkyl and amide, e.g., —$(CH_2)_4$—, m is selected from Tc and Re, and n ranges from about 50 to about 500. Carboxymethyl dextran 1 is reacted with a chelate compound 2 that is formed as described below. Alpha-t-BOC-lysine is condensed with bromo- (or iodo-) acetic acid N-hydroxy succinimidyl (NHS) ester to give epsilon-bromoacetamido-alpha-BOC lysine. Conversion of the epsilon-bromoacetamido-alpha-BOC lysine to an NHS ester by reaction with NHS and DCC. Condensation with glycine affords epsilon-bromoacetamido-alpha-BOC-lysyl-glycine. Conversion of the glycine compound to the NHS ester derivative (e.g., with NHS and DCC) followed by condensation with aminoethanol provides epsilon-bromoac-etamide-alpha-BOC-lysyl-glycol-amidoethanol. BOC cleavage with trifluoroacetic acid and condensation with S-ethoxy-ethyl mercapto-acetic acid NHS ester results in a S-ethoxyethyl-mercaptoacetyl-epsilon-bromoacetamido-lysyl-glycyl-amidoethanol chelate compound. The chelate is complexed with rhenium using standard labeling conditions described above (e.g., aqueous perrhenate solution reduced with tin chloride in the presence of citric acid) to form 2. 1 and 2 are coupled using carbodiimide EDCI (1,3-dimethylaminopropyl)-3-ethyl carbodiimide hydrochloride) to form metal-chelate-dextran conjugate 3. 3 is conjugated to an antibody thiol group to displace the bromide on the chelate and give the thioether-antibody-radiolabeled chelate-dextran conjugate 4.

B. From Dextran Hydrazide. The reaction scheme for this synthesis is shown below.

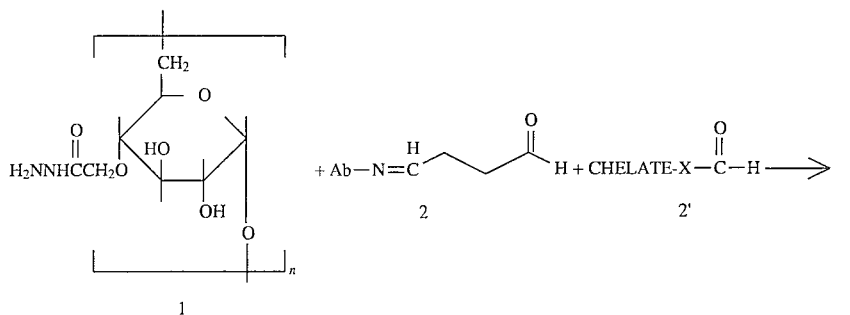

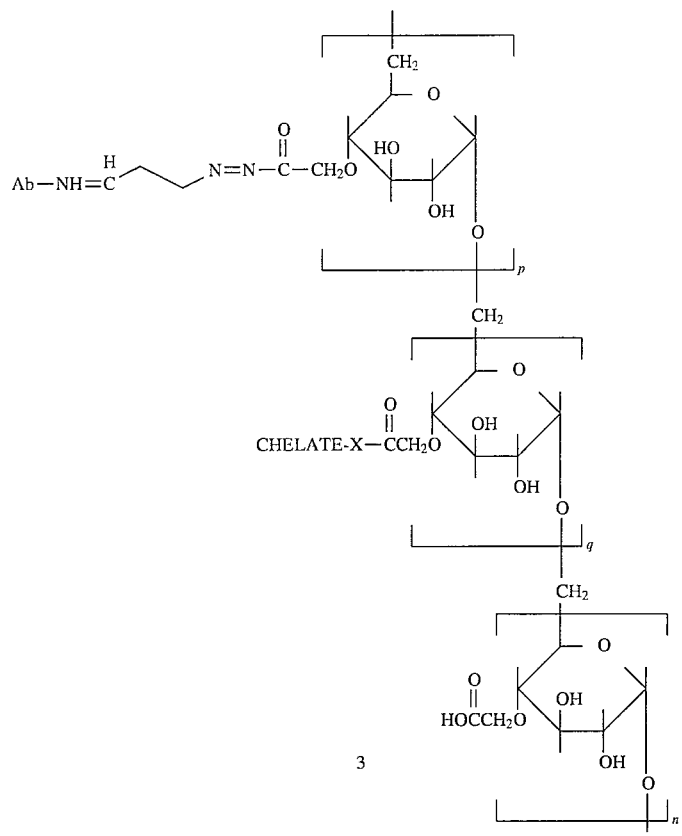

where X is selected from —(CH$_2$)$_r$—, —NHCO(CH$_2$)$_r$—; r ranges from about 1 to about 10; n ranges from about 50 to about 500, p ranges from about 0.5 to about 1, and q ranges from about 49 to about 499. Dextran hydrazide 1 is conjugated to antibody aldehyde 2 and chelate-aldehyde 2' to form dextran hydrazone conjugate 3 substantially in accordance with the methodology employed by Hurwitz et al., *J. Med. Chem.*, 28,:137, 1985, in the preparation of an antibody-dextran-5-FU conjugate. Antibody aldehydes 2 are formed by condensation of antibody amines with glutaraldehyde in accordance with known techniques therefor to give the antibody imine conjugate having a terminal aldehyde moiety. Chelate aldehyde 2' synthesis is shown below:

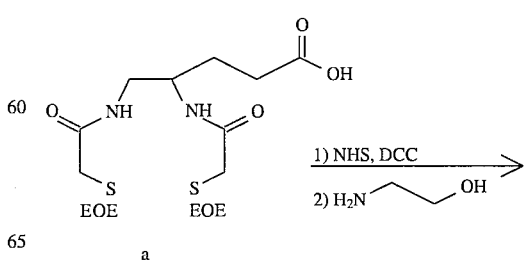

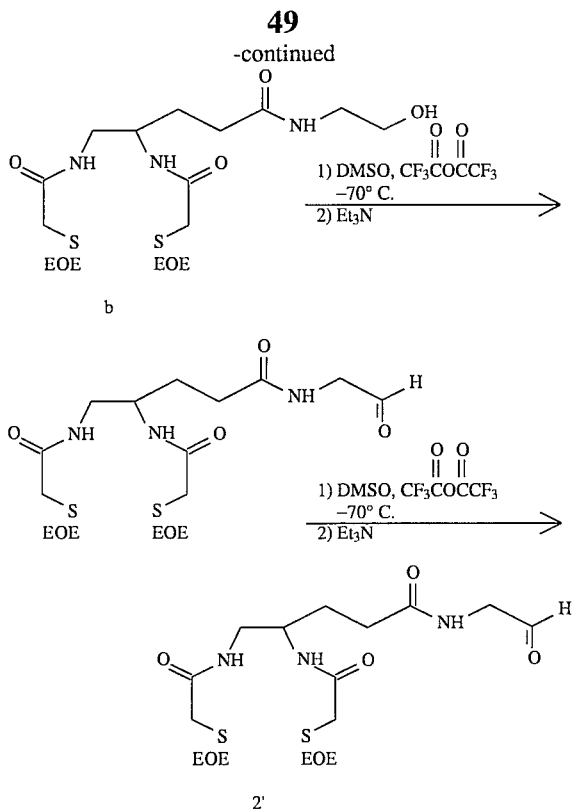

Chelate $C_5N_2S_2$ carboxylic acid a is condensed with NHS, DCC to give the chelate NHS ester. The NHS ester is condensed with aminoethanol to provide chelate-amidoethanol b. Swern oxidation of b with DMSO and trifluoroacetic anhydride provides chelate aldehyde 2'.

EXAMPLE VI

Somatostatin Derivative (Octreotide)-Dextran Synthesis

A. From Dextran Hydrazide. Briefly, suitably blocked octreotide, i.e., with the lysine amino (trifluoroacetamidolysine for subsequent cleavage with piperidine) and both threonine hydroxy groups blocked, is acylated at the amino terminus by condensation with a chelate active ester, such as a tetrafluorophenyl ester in DMF and triethylamine. The resultant chelate-octreotide is activated with carbodiimide or converted to the N-hydroxysuccinimide ester and condensed with dextran hydrazide to give the acylhydrazide chelate-octreotide-dextran product.

B. From Carboxymethyl Dextran. A BOC-amino protected, trifluoroacetamide-lysine-octreotide carboxy succinimidyl ester is prepared in accordance with known procedures therefor. See, for example, UK Patent Application GB 2 225 579. The ester is condensed with chelate amine to provide chelate linked to the octreotide carboxy terminus by an amide linkage. Subsequent cleavage of the N-BOC protecting group with trifluoroacetic acid is undertaken. The resultant amine is condensed with carboxymethyl dextran using carbodiimide coupling chemistry (i.e., carboxymethyl dextran previously activated with EDCI) provides chelate-octreotide-carboxymethyl dextran with the octreotide amino terminus linked to the dextran carboxy moiety by an amide linkage.

C. From Oxidized Dextran. Dextran aldehyde is prepared by periodate oxidation of dextran. The octreotide amino terminus is linked by an amide linkage to a chelate carboxyl group by coupling suitably blocked octreotide to a chelate active ester, such as a trifluorophenyl ester. The carboxy terminus of octreotide is then converted to the methyl ester for conversion to a hydrazide upon reaction with hydrazine. It is worthy of note that the preparation of the chelate-octreotide-hydrazide can be conducted by first generating the carboxy terminus hydrazide and subsequently coupling the amino terminus to the chelate active ester. Conjugation of chelate-octreotide-hydrazide to the polyaldehyde dextran provides the acyl hydrazone product.

C. From Aminodextran. Methods of introducing amino groups on dextran are known. For example, Noguchi et al., Bioconj. Chem., 3:132–137, 1992, suggests introducing a spacer through an ether linkage to a dextran hydroxyl group by reacting dextran with 6-bromohexanoic acid under basic conditions (4M NaOH at 80° C. for 3 hours). Next, ethylenediamine is reacted with the carboxyl group of the spacer arm of the dextran backbone using EDCI at pH 5. Another method for amino group introduction is discussed in Mann et al., Bioconj. Chem., 3:154, 1992. In this method, a dextran hydroxy group is derivitized with acrylonitrile. The nitrile is subsequently reduced to form the amino dextran derivative.

The octreotide amino terminus is linked by an amide linkage to a chelate carboxyl group by coupling octreotide to a chelate active ester, such as a trifluorophenyl ester. The carboxy terminus of octreotide is then activated with EDCI and reacted with aminodextran to form an amide linkage between the dextran amine and the octreotide carboxy terminus and a chelate-octreotide-dextran product.

EXAMPLE VII

Synthesis of DTPA/Biotin/Radionuclide Conjugate

A. Synthesis-1 of DTPA-Biotin-Radionuclide. The synthesis of DTPA-biotin-radionuclide conjugate proceeds as follows:

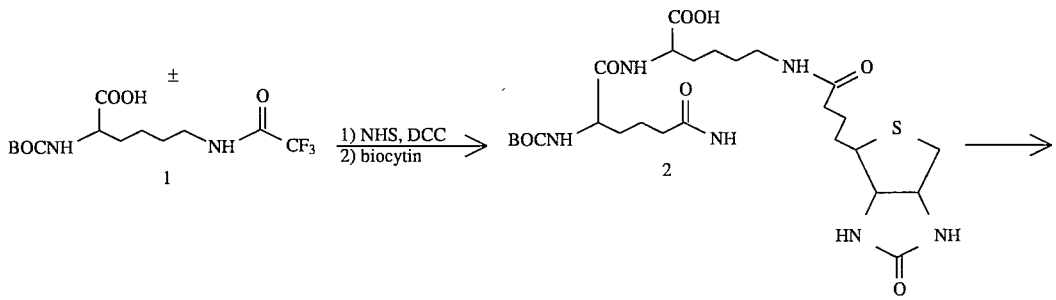

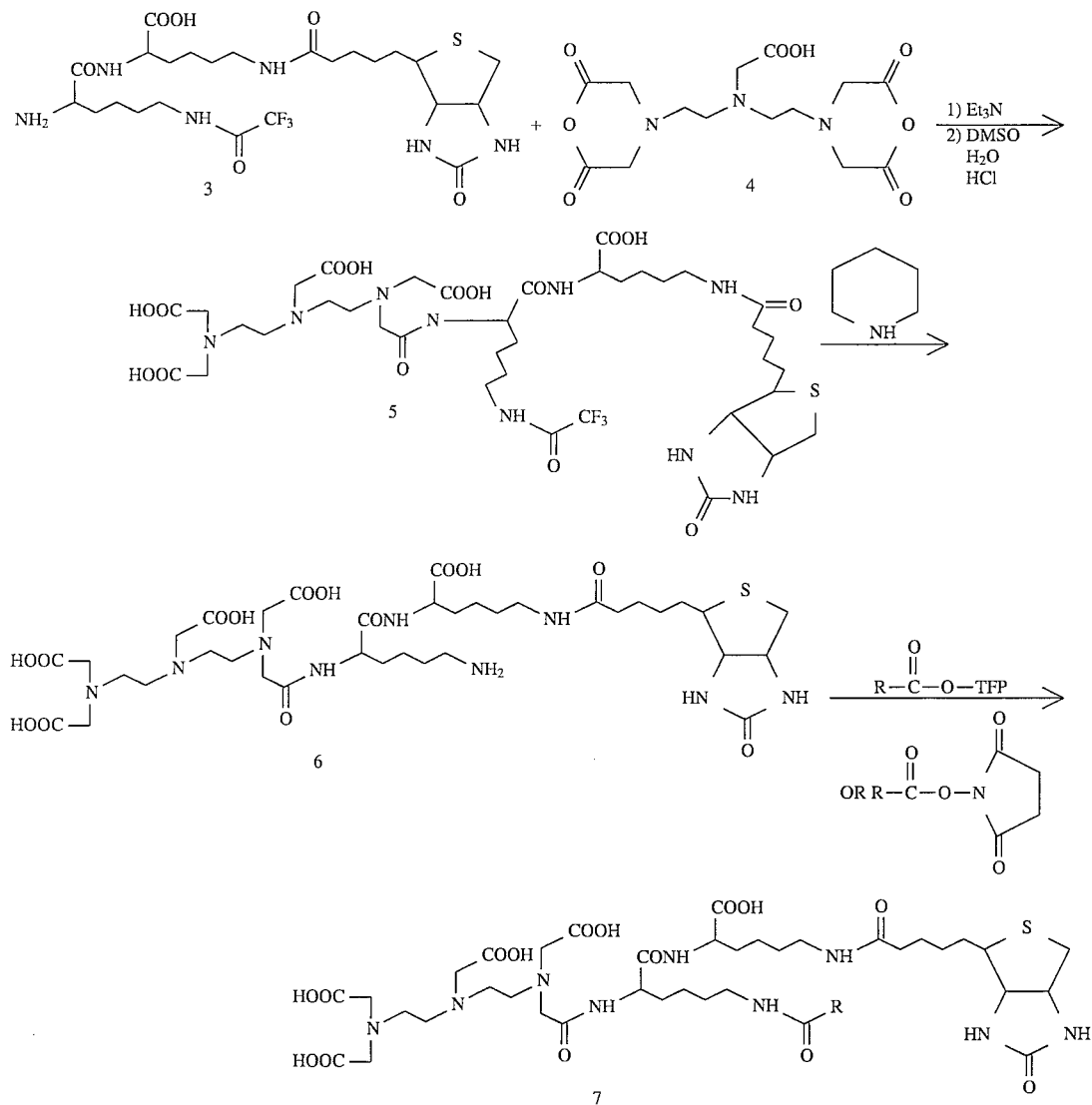

N-alpha-BOC-N-epsilon-trifluoroacetamide (TFA)-lysine 1 was converted to a N-hydroxysuccinimidyl ester with NHS and DCC and then condensed with biocytin free base. The alpha amino group of the resultant lysylbiocytinamide derivative 2 was selectively deprotected with trifluoroacetic acid. A 5 molar excess of DTPA- dianhydride was added to the selectively deprotected product 3 to maximize the formation of the monoamide adduct 5. The epsilon-TFA group of the DTPA-lysylbiocytinamide 5 was cleaved with piperidine to form an amine 6, which is acylated with N-hydroxysuccinimidyl p-iodobenzoate to give the iodinated final product 7 (R is p-iodophenyl). Alternatively, Re-chelate-DTPA conjugate 7 is formed by acylation of the amino with Re-complexed chelate, Re-oxomercaptoacetylglycylglycyl-gamma-amino butyric acid tetrafluorophenyl ester.

(1) Synthesis of alpha-N-BOC-epsilon-N-trifluoroacetamido-lysine-biocytinamide 2. N-hydroxysuccinimide (486 mg, 4.22 mmol) and DCC (870 mg, 4.22 mmol) were added to an ice cold solution of N-alpha-BOC-N-epsilon-TFA-lysine (Bachem, Torrance, Calif.) (1.156 g, 3.38 mmol) in acetonitrile (7.0 ml). The reaction was warmed to 23° C. and stirred for 1 hour. Glacial acetic acid (10 drops) was added to quench excess DCC. The reaction mixture was filtered. The filtrate was evaporated to give the N-alpha-BOC-N-epsilon-TFA-lysine succinimidyl ester as a white solid (1.43 g, 100% yield). The product was used without purification. The product and biocytin (1.38 g, 3.71 mmol) were suspended in DMSO (15 ml). The suspension was heated at 118° for 15 minutes until all the solids dissolved. The solution was applied to a 45 mm column (Kontes) filled to a height of eight inches with C-18 reverse phase silica (VWR). The column was eluted with one bed volume each of 80%, 40% and 50% methanol/water. The product was obtained in 56% yield.

$^1$H NMR (DMSO): 1.20–1.80 (m, 21H, alkyl CH$_2$), 2.05 (t, 2H, CH$_2$CO), 2.75 (dd, 2H, SCH$_2$), 3.05 (dd, 2H, CH$_2$NHCO), 3.15 (dd, 2H, CH$_2$NHTFA), 3.90 (broad s, 1H, CHNHBOC), 4.15 (m, 2H, 2×CHN), 4.32 (m, 1H, CHN), 6.35 (s, 1H, NHCONH), 6.42 (s, 1H, NHCONH), 6.85 (d, 1H, NHBOC), 7.75 (t, 1H, HNCO), 7.95 (d, 1H, NHCO), 9.40 (t, 1H, NHTFA). Proton assignment was confirmed by decoupling experiments.

(2) Synthesis of epsilon-trifluoroacetamido-biocytinamido lysine 3. 10 ml of a 50% methylene chloride: triflouroacetic acid solution was added to 0.94 g of 2. The solution was stirred at 23° C. for 1 hour, then evaporated. The residue was purified by reverse phase C-18 flash chromatography to give 3 as a fluffy white solid, quantitative yield.

¹H NMR (DMSO): 1.20–1.80 (m, 18H, alkyl CH₂), 2.05 (t, 2H, CH₂CO), 2.70 (dd, 2H, SCH₂), 3.3–3.85 (m, integration obscured by water in DMSO), 4.05–4.35 (m, 4H, 4×CHN), 6.40 (broad d, 2H, NHCONH), 7.80 (t, 1H, HNCO), 8.15 (m, 3H, NH₃), 8.65 (d, 1H, NHCO), 9.40 (t, 1H, NHTFA).

(3) Synthesis of biocytinamido-epsilon-trifluoroacetamido-N-DTPA-lysine amide 5. Triethylamine (0.44 ml, 3.19 mmol) was added to a solution of 3 (54 mg, 0.79 mmol) in DMSO (3.0 ml). Diethylene triamine pentaacetic acid dianhydride (DTPA) (1.03 g, 3.19 mmol) was added all at once to the reaction solution. The reaction was stirred at 23° C. for 90 minutes and then quenched by the addition of water (5.0 ml). Stirring was continued for 45 minutes. The mixture was filtered. The solid was washed with 50% methanol/water and then methanol (50 ml of each). The filtrate was evaporated, and the residue was purified by reverse phase C-18 flash chromatography to give 5 as a white solid in 43% yield.

¹H NMR ( DMSO): 1.10–1.80 (m, 18H, alkyl CH₂), 2.80–4.0 (m, integration not calculated because of overlapping solvent peaks), 4.15 (m, 1H, CHN), 4.25 (m, 1H, CHN), 6.35 and 6.45 (2×s, 2×1H, NHCONH), 7.85 (t, 1H, HNCO), 8.25 (d, 1H, NHCO), 8.40 (d, 1H, NHCO), 9.70 (t, 1H, NHTFA). Single peak on reverse phase HPLC, retention time 27.6 min with a gradient t=0, 30% A, 70% B; t=60 min, 100% A where A=60% CH₃CN/H₂O 0.1% TFA and B=99.9% H₂O, 0.1% TFA.

(4) Synthesis of biocytinamido-N-alpha-DTPA-lysine amide 7. A solution of 1M piperidine in THF/H₂O, 1:1 (5.0 ml) was added to solid 5 (100 mg). The reaction solution was stirred at 23° C. for 60 hours, acidified by the addition of glacial acetic acid and concentrated. The residue was purified by reverse phase flash chromatography twice. The produce (32 mg) was obtained as a white solid in 35% yield.

¹H NMR (DMSO): 1.20–1.80 (m), 2.05 (t, CH₂CO), 2.80–4.15 (broad multiplet obscured by water in DMSO), 4.15 (m, CHN), 4.35 (m, 1H, CHN), 6.40 and 6.55 (2 singlets, NHCONH), 8.00 (broad s, HNCO), 8.15 (broad s, NHCO), 9.05 (broad s, NHCO). Single peak on reverse phase HPLC, retention time 7.94 min with a gradient t=0, 30% A, 70% B; t=60 min, 60% A, 40% B where A=60% CH₃CN/H₂O 0.1% TFA and B=99.9% H₂O, 0.1% TFA.

B. Synthesis-2 of DTPA-Biotin-Radionuclide.

Alternatively, the synthesis of DTPA-biotin-radionuclide conjugate proceeds as follows:

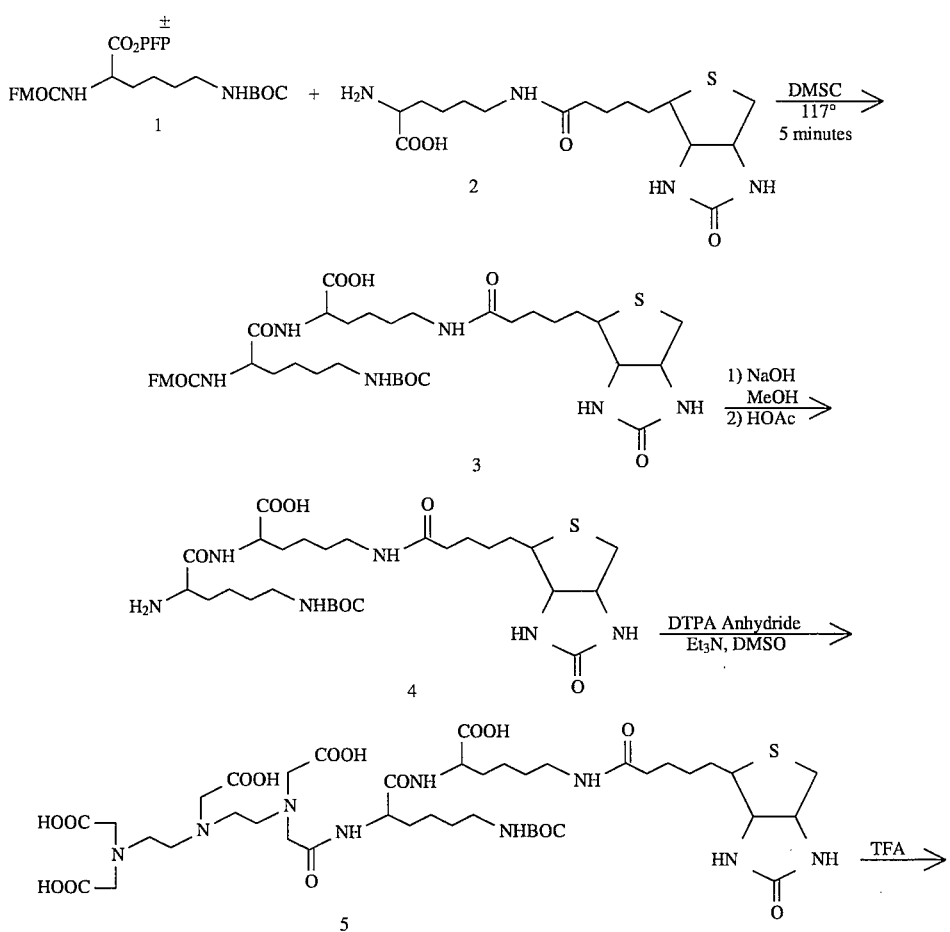

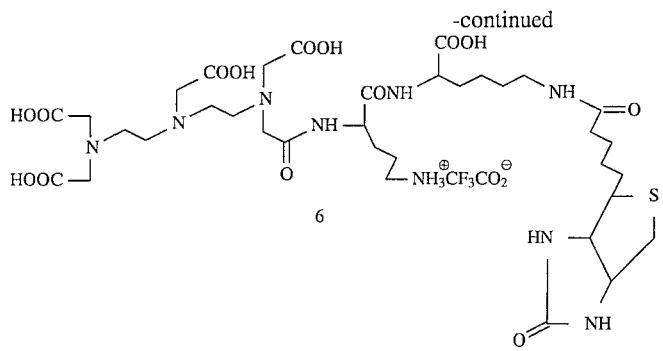

A solution of N-alpha-FMOC-N-epsilon-BOC-lysine pentafluorophenyl ester 1 and biocytin 2 in DMSO was heated at 117° for 5 minutes to give N-alpha-FMOC-N-epsilon-BOC lysylbiocytinamide 3. The FMOC group was cleaved by dissolving 3 in a 1:1 solution of 2N NaOH:MeOH and stirring at room temperature for 20 minutes. The reaction solution was washed with toluene to remove FMOC reagent byproduct. The aqueous layer was evaporated to give the amine 4 which was used in the next reaction step without purification. A solution of 4 and a 5 molar excess of DTPA-dianhydride with triethylamine in DMSO is stirred at room temperature to give the monoamide 5. Deprotection of the epsilon-BOC amine with trifluoroacetic acid affords the final product 6.

(1) Synthesis of alpha-N-FMOC-epsilon-BOC-lysyl biocytinamide 3. A mixture of alpha-N-FMOC-epsilon-BOC-lysine pentafluorophenyl ester (1.153 g, 1.82 mmol) (Sigma Chemical Company) and biocytin (0.75 g, 2.00 mmol) (Sigma Chemical Company) in DMSO (8.0 ml) was heated at 117° C. for 5 minutes until all of the solids dissolved. The product was purified by reverse phase C-18 flash chromatography (45 mm column packed with 8 inches of C-18 silica, eluted with one bed volume each of 30%, 50% and 70% methanol/water) to give 3 as a white solid (0.889 g) in 59% yield.

$^1$H NMR (DMSO): 1.15–1.80 (m, 27H, OC(CH$_3$)$_3$ and alkyl CH$_2$ groups), 2.05 (t, 2H, CH$_2$CO), 2.75 (dd, 2H, SCH$_2$), 2.85–3.15 (m, 4H, CH$_2$NCO×2), 3.98–4.47 (m, 6H, CHN×4, FMOCCH$_2$), 6.35 (s, 1H, NHCO), 6.45 (s, 1H, NHCO), 6.80 (t, 1H, HNCO), 7.30–7.55 (m, 5H), 7.70–8.25 (m, 6H).

(2) Synthesis of epsilon-BOC-lysyl biocytinamide 4. A 1:1 solution of 2N NaOH and methanol (12.0 ml) was added to 3 (231 mg, 0.28 mmol). The suspension was stirred at 23° C. for 30 minutes. The stirred suspension was acidified by the addition of glacial acetic acid and concentrated. The residue was partitioned between toluene and water. The aqueous layer was evaporated to give 4 containing NaCl.

$^1$H NMR (D$_2$O): 1.30–2.00 (m, 27H, OC (CH$_3$)$_3$ and alkyl CH$_2$ groups), 2.35 (t, 2H, CH$_2$CO), 3.05 (dd, 2H, SCH$_2$), 3.10–3.25 (m, 4H, NCH$_2$×2), 3.35 (dd, 1H, CHS), 4.05 (dd, 1H, CHN), 4.55 (dd, 1H, CHN, 4.65 (dd, 1H, CHN).

C. Synthesis of Radionuclide-DTPA-Biotin. The preparation of Radionuclide-DTPA-Biotin conjugates proceeds as shown below:

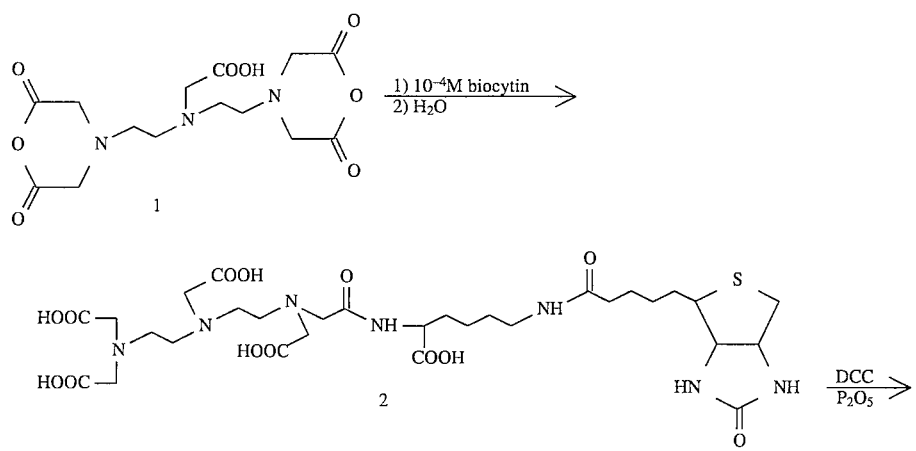

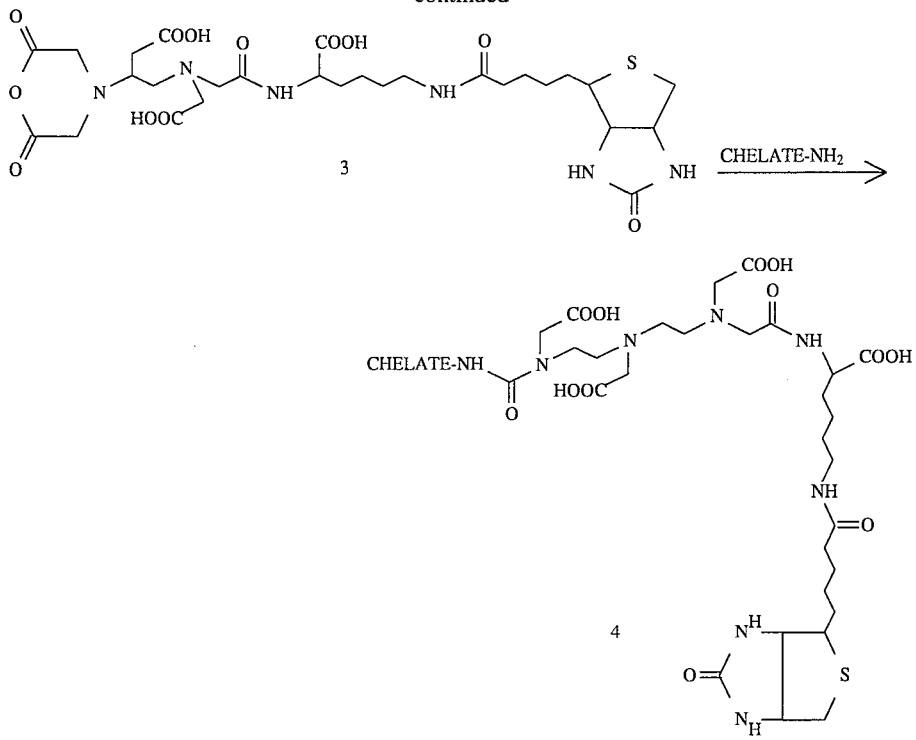

DTPA-dianhydride 1 is opened with biocytin using high dilution and simultaneous reactant addition techniques discussed in Paik et al., *J. Nucl. Med.*, 30: 1693–1701, 1989. The monoamide adduct 2 is isolated and purified by chromatography to remove unreacted DTPA and the diamide adduct. The terminal carboxylates of 2 are cyclized by dehydration in the presence of DCC and $P_2O_5$ to form the anhydride 3. Chelate-$NH_2$ is employed to open the anhydride of 3 to form the chelate-DTPA-biotin product 4. Alternatively, 1 may be opened with chelate-$NH_2$ and the anhydride group of 3 may be opened with biocytin in the formation of the product 4.

EXAMPLE VIII

Radiolabeled DTPA-Antibody Conjugate Synthesis

The strategy for the preparation of a radiolabeled DTPA-antibody conjugate involves attachment of a ligand active ester to an ethylene diamine spacer which is attached to the carboxyl group of lysine. One lysine amino group is attached to a DTPA carboxylate. The remaining lysine amino group is acylated with bromoacetic acid NHS ester for subsequent attachment of antibody thiols. Thus, displacement of the bromide provides a thioether bond to the antibody.

N-alpha-FMOC (fluorenomethyl)-lysine (Bachem, Torrance, Calif.) is condensed with bromoacetic acid N-hydroxysuccinimidyl ester to give epsilon-bromoacetamido-N-alpha-TFA-lysine. Conversion to the N-hydroxysuccinimidyl ester is accomplished by reacting the compound with NHS and DCC. Condensation with S-ethoxyethylmercaptoacetyl-glycylglycyl-gamma-aminobutyryl ethylene diamine (formed by reacting a tetrafluorophenyl ester of S-ethoxyethylmercaptoacetyl-glycylglycyl-gamma-aminobutyric acid with ethylene diamine in $CH_3CN$) provides $N_3S$ chelate-lysine bromoacetamide. Deprotection of the amine by reaction with piperidine provides a free amine for reaction with DTPA dianhydride. This reaction opens the DTPA dianhydride and provides a DBM-chelate conjugate having a DTPA carboxylate attached by an amide linkage to a lysine amino group associated with the chelate. The $N_3S$ core is radiolabeled with rhenium under the post-formed reaction conditions described above. The rhenium-chelate-DTPA conjugate is conjugated to an antibody thiol group by displacement of the bromide to form a thioether bond, also as described above.

EXAMPLE IX

Radiolabeled Polyglutamyl-Antibody Conjugate Synthesis

A. Antibody-DBM Stable Linkage. The N-terminus of the polyglutamyl molecule is acylated with N-t-BOC glycine-N-hydroxy-succinimidyl ester to give polyglutamic acid monofunctionalized with a protected amine. The protected amine permits selective terminal monofunctionalization to a reactive isothiocyanato group for attachment to a single antibody. A polymer molecule bearing a uniquely reactive terminus for univalent attachment to biomolecules overcomes the problem of crosslinking antibodies and resultant aggregation as discussed in Mann et al., *Bioconjugate Chem.*, 3:154–159, 1992.

The BOC-glycineamidopolyglutamic acid derivative is then coupled to a chelate-amine, e.g., S-ethoxyethylmercaptoacetyl-glycylglycyl-gamma-aminobutylamidoethylenediamine as described above, using EDCI as a coupling agent to give a polyglutamic acid derivative with n carboxylates attached to chelate amino groups and p free carboxylates. The chelate is labeled with rhenium under standard conditions therefor as described above. The BOC protecting group of the DBM-chelate conjugate is cleaved with formic acid, with the resultant free amino group being converted to an isothiocyanate with thiophosgene in bicarbonate. An antibody amino group is coupled to the isothiocyanate under basic conditions to give the thiourea-linked antibody-DBM-chelate conjugate. Such conjugates have a stable antibody-DBM linkage.

B. Antibody-DBM Acid Labile Linkage. BOC-polyglutamic acid is coupled to a chelate amino group using EDCI to give N-BOC-polyglutamate-chelate conjugate. This conjugate contains n carboxylates attached to chelate amino groups and p free carboxylates. Formic acid deprotection of the BOC group and condensation with N-BOC(hydroxylamino)acetic acid NHS ester gives the BOC-protected terminal alkoxy amino polyglutamate-chelate conjugate. The chelate is labeled with rhenium under standard conditions therefor as described above. BOC-deprotection with formic acid and condensation with antibody aldehyde gives a alkoximine-linked antibody-DBM-chelate conjugate.

Alternatively, Cbz (carbobenzyloxy) groups may be employed as protecting groups in the synthesis of alkoximine linked antibody-DBM-containing conjugates. When Cbz groups are employed, trimethylsilyliodide is used in the deprotection reaction.

The alkoximine linker is susceptible to hydrolysis in the liver as well as in the acidic environment produced by lysosomes inside target cells (e.g., tumor cells). Provided the antibody-DBM-chelate conjugates exhibit good serum stability, improved targeting is expected with alkoximine-linked conjugates.

C. Antibody-DBM Enzyme Cleavable Linkage. Mono-t-butylsuccinate is coupled to Cbz-aminoethanol with isopropenyl chlorocarbonate ($Et_3N$, DMAP) to give a t-butyl aminoethyl succinate ester. Trifluoroacetic acid cleavage of t-butyl ester and activation with NHS and DCC provides a 2-Cbz-aminoethyl-mono-NHS succinate ester. The NHS ester is coupled to polyglutamic acid to form an N-terminal functionalized polyglutamate derivative. The carboxyl groups of polyglutamate are activated with EDCI and coupled to chelate amine groups. The chelate is labeled with rhenium under standard conditions therefor as described above. Trimethylsilyliodide cleavage of the Cbz protecting group provides a free amino group which can either be directly coupled to antibody aldehyde groups or converted to an isothiocyanate with thiophosgene. The latter protocol is completed by formation of a thiourea conjugate by reacting an antibody amino group with the DBM isothiocyanate moiety.

This conjugate of the present invention exhibits monofunctionalization of the N-terminus of the DBM, the advantage of which (prevention of the formation of cross-linked conjugates) having been discussed above. The aminoethyl ester linker is expected to be susceptible to esterases in the liver and kidney. Cleavage of this linker releases the radioactivity on the DBM (i.e., decouples the radioactivity from the antibody targeting moiety).

EXAMPLE X

Radiolabeled Polyglutamyl-Biotin Conjugate Synthesis

A polyglutamate amine group is acylated with biotin-NHS ester which is prepared in accordance with conventional chemistry therefor or obtained from Sigma Chemical Company. This acylation results in an amide-linked DBM-ligand conjugate. Polyglutamate carboxylates are then activated with EDCI and coupled to chelate amine groups to form the product chelate-DBM-ligand conjugate. Optionally, additional biotin molecules can be linked to the DBM by coupling EDCI-activated polyglutamyl carboxylates to biocytin. The chelate is labeled with radionuclide under standard conditions therefor.

EXAMPLE XI

Radiolabeled Succinylated Polylysine-Biotin Conjugate Synthesis

Chelate-succinylated polylysine-biotin conjugates are preparable in accordance with the reaction scheme shown below:

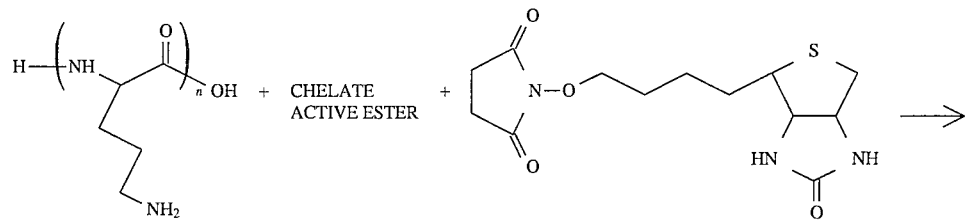

-continued

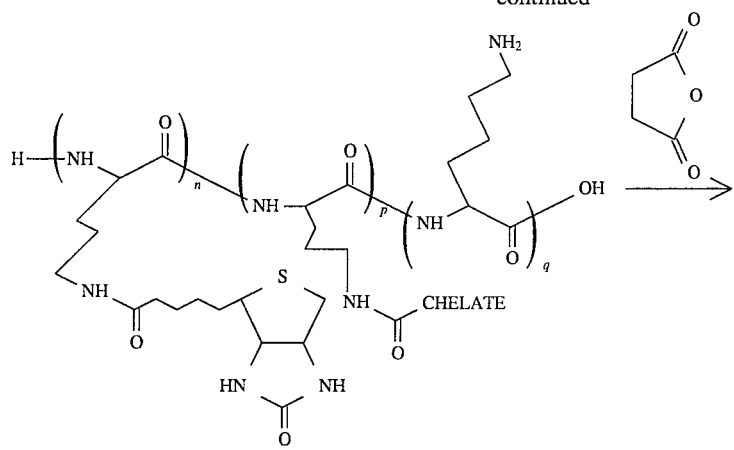

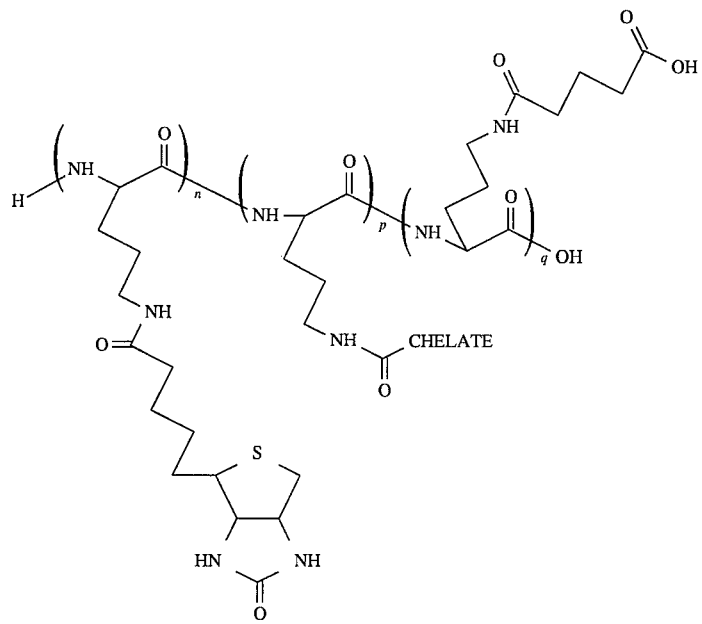

Polylysine is acylated with p moles of chelate active ester to form a DBM (polylysine)-chelate conjugate. The DBM-chelate conjugate is then acylated with n moles of biotin NHS ester to form a biotin-DBM (polylysine)-chelate conjugate. The remaining amino groups of polylysine are capped with succinic anhydride to form a biotin-DBM (succinylated polylysine)-chelate conjugate.

EXAMPLE XII

Targeted, Direct Labeled Protocol

A patient is suspected of having lung cancer. A NR-LU-10 monoclonal antibody, specific for a pancarcinoma antigen, is conjugated to carboxymethyl dextran. The antibody-DBM conjugate is further derivitized with 3–5 chelates, which have been previously radiolabeled with a diagnostic radionuclide, to form an antibody-DBM-(radionuclide chelate)$_{3-5}$ conjugate. The final conjugate is administered to the patient in a diagnostically effective dose and in a pharmaceutically acceptable diluent. The antibody directs the conjugate to the target site, while the DBM directs the biodistribution of non-targeted conjugate and metabolites thereof.

EXAMPLE XIII

Three-Step Pretargeting

A patient has ovarian cancer. A monoclonal antibody directed to an ovarian cancer cell antigen is conjugated to biotin to form a MAb-biotin conjugate. The MAb-biotin conjugate is administered to the patient in an amount in excess of the maximum tolerated dose of conjugate administerable in a targeted, direct label protocol and is permitted to localize to target cancer cells for 24–48 hours. Next, an amount of avidin sufficient to clear non-targeted MAb-biotin conjugate and bind to the targeted biotin is administered. A biotin-dextran-radionuclide chelate conjugate of the type discussed in Examples II–IV above is dispersed in a pharmaceutically acceptable diluent and administered to the patient in a therapeutically effective dose. The biotin-dextran-radionuclide chelate conjugate localizes to the targeted MAb-biotin-avidin moiety or is removed from the patient via the renal pathway.

EXAMPLE XIV

Two-Step Pretargeting

A patient has colon cancer. A monoclonal antibody directed to a colon cancer cell antigen is conjugated to streptavidin to form a MAb-streptavidin conjugate. The MAb-streptavidin conjugate is administered to the patient in an amount in excess of the maximum tolerated dose of conjugate administerable in a targeted, direct label protocol and is permitted to localize to target cancer cells for 24–48 hours. A biotin-DTPA-radionuclide chelate conjugate of the type discussed in Example VII above is dispersed in a pharmaceutically acceptable diluent and administered to the patient in a therapeutically effective dose. The biotin-DTPA-radionuclide chelate conjugate localizes to the targeted MAb-streptavidin moiety or is removed from the patient via the renal pathway.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method of providing for enhanced renal excretion of radionuclides via the renal pathway, which radionuclides are used in a diagnostic or therapeutic protocol for the treatment or diagnosis of a mammalian subject, which method comprises administering a conjugate comprising:

(i) a directed biodistribution molecule which is specifically excreted via a renal pathway selected from the group consisting of dextran and inulin, (ii) biotin conjugated or complexed to said directed biodistribution molecule; and (iii) a radionuclide, and wherein said conjugate does not comprise an antibody or an antibody fragment.

2. The method of claim 1 wherein the directed biodistribution molecule is dextran.

3. The method of claim 1 wherein the directed biodistribution molecule is inulin.

4. The method of claim 1 wherein the radionuclide is selected from the group consisting of gamma-emitters, positron-emitters, Auger electron-emitters, X-ray emitters, fluorescence-emitters, alpha-emitters and beta-emitters.

5. The method of claim 4 wherein the radionuclide is selected from the group consisting of $^{123}$I, $^{125}$I, $^{130}$I, $^{131}$I, $^{133}$I, $^{135}$, $^{47}$Sc, $^{72}$As, $^{72}$Se, $^{90}$Y, $^{88}$Y, $^{97}$Ru, $^{100}$Pd, $^{101m}$Rh, $^{119}$Sb, $^{128}$Ba, $^{197}$Hg, $^{211}$At, $^{212}$Bi, $^{153}$Sm, $^{169}$Eu, $^{212}$Pb, $^{109}$Pd, $^{111}$In, $^{67}$G, $^{68}$Ga, $^{67}$Cu, $^{75}$Br, $^{76}$Br, $^{77}$Br, $^{99m}$Tc, $^{11}$C, $^{13}$N, $^{15}$O, $^{18}$F, $^{188}$Re, $^{186}$Re, $^{203}$Pb, $^{212}$Pb, $^{64}$Cu, $^{105}$Rh, $^{198}$Au, $^{199}$Au, and $^{177}$Lu.

6. The method of claim 5 wherein the radionuclide is $^{125}$I.

* * * * *